US009625467B2

(12) United States Patent
Zhao

(10) Patent No.: US 9,625,467 B2
(45) Date of Patent: Apr. 18, 2017

(54) AGENT AND METHOD FOR IDENTIFYING LYSINE CROTONYLATION IN PROTEINS

(75) Inventor: Yingming Zhao, Chicago, IL (US)

(73) Assignee: PTM BIO LLC, Chicago, IL (US)

( * ) Notice: Subject to any disclaimer, the term of this patent is extended or adjusted under 35 U.S.C. 154(b) by 1531 days.

(21) Appl. No.: 13/117,154

(22) Filed: May 27, 2011

(65) Prior Publication Data

US 2012/0135538 A1   May 31, 2012

Related U.S. Application Data

(60) Provisional application No. 61/349,185, filed on May 27, 2010.

(51) Int. Cl.
*G01N 31/00* (2006.01)
*G01N 33/53* (2006.01)
*G01N 33/68* (2006.01)
*C07K 16/44* (2006.01)

(52) U.S. Cl.
CPC ......... *G01N 33/6803* (2013.01); *C07K 16/44* (2013.01)

(58) Field of Classification Search
CPC ........ A61K 47/48784; A61K 47/48215; A61L 27/52; C12N 2501/585; G01N 33/6875; C07H 21/04
See application file for complete search history.

(56) References Cited

U.S. PATENT DOCUMENTS

| 6,958,212 B1 * | 10/2005 | Hubbell et al. ............ 424/78.17 |
| 7,485,416 B2 | 2/2009 | Ott et al. |
| 7,744,912 B1 * | 6/2010 | Hubbell et al. ............... 424/422 |
| 2012/0135538 A1 | 5/2012 | Zhao |

FOREIGN PATENT DOCUMENTS

| EP | 2 562 264 A1 | 2/2013 |
| WO | WO 03/070394 A2 | 8/2003 |
| WO | WO 2011/132392 A1 | 10/2011 |

OTHER PUBLICATIONS

Sluti et al., Gene-Specific Characterization of Human Histone H2B by Electron Capture Dissociation, Journal of Proteome Research, 2006, 5, 233-239.*
Siuti et al. Journal of Proteome Research, 2006, vol. 5, pp. 233-239.*
Bao et al., eLIFE, pp. 1-18 (2014).
Bonenfant et al., Molecular & Cellular Proteomics, 5.3:541-52 (2006).
Boyne et al., Journal of Proteome Research, 5:248-53 (2006).
Chen et al., J Proteome Res. 4(3):998-1005 (2005).
Chen et al., PNAS, 106(3):761-66 (2009).
Chu et al., Mol & Cell Proteomics, 5.1:194-203 (2006).
Cosgrove et al., Nat Struct Mol Biol, 11:11:1037-43 (2004).
European Search Report, Appl. No. EP 12 19 9554, dated Mar. 18, 2013.
Garcia et al., Curr Opin Chem Biol, 11:66-73 (2007).
Garcia et al., Nat Methods, 4:6:487-89 (2007).
Garcia et al., Nat Protoc, vol. 2:4:933-38 (2007).
Gattner et al., Chem Commun., 49:379-81 (2013).
Jenuwein and Allis, Science, 293:1074-80 (2001).
Johnson et al., Nucleic Acids Res, 32(22):6511-18 (2004).
Kehoe et al., Research, 5.12:2350-63.
Kim et al., Mol Cell 23:607-18 (2006).
Kouzarides, Cell 128:693-705 (2007).
Liu et al., Arthritis Research & Therapy, 14:R25, pp. 1-14 (2012).
Luo et al., J Biol Chem, 283(28)19176-183 (2008).
Margueron et al., Curr Opin Genet Dev., 15:163-76 (2005).
Martin and Zhang, Curr Opin Cell Biol., 19:266-72 (2007).
Medzihradszky et al., Molecular & Cellular Proteomics 3.9:872-86 (2004).
Mersfelder and Parthun, Nucleic Acids Res., 34(9):2653-62 (2006).
Montellier et al., Bioessays, 34:187-93 (2011).
Ruthenburg et al., Nat Rev Mol Cell Biol., 8:983-94 (2007).
Sakabe et al., PNAS, 107(46):19915-920 (2010).
Shechter et al., Nat Protoc, 2(6):1445-57 (2007).
Tan et al., Cell 146:1016-28 (2011).
Tateishi et al., Nature, 458:757-61 (2009).
Venter et al., Science, 291:1304-52 (2001).
Wiśniewski et al., Mol. Cell Proteomics, 6.1:72-87 (2007).
Wysocka et al., Cell, 121:859-72 (2005).
Wysocka et al., Nature, 442:86-90 (2006).
Zee et al., J Biol Chem, 285(5)3341-350 (2010).
Zeng and Zhou, FEBS Letters, 513:124-28 (2002).
Zhang et al., J Proteome Res, 9(1):585-94 (2010).
Gattner et al., Electronic Supplementary Material (ESI) for Chemical Communications, pp. 1-30 (2013).
Office Action in U.S. Appl. No. 13/531,282 issued by USPTO on Feb. 13, 2017.
PTM Biolabs, Pan anti-butyryllysine antibody, https://www.ptmbiolabs.com/product/ptm301/, 7 pages (2017).
Zhang et al., Journal of Proteome Research, 8:900-6 (2009).

\* cited by examiner

*Primary Examiner* — Lisa Cook
(74) *Attorney, Agent, or Firm* — RatnerPrestia

(57) ABSTRACT

A method and related agent for detecting novel post-translational modification. This novel post-translational modification is in the form of crotonylation of lysine residues in proteins. The method includes the steps of (a) preparing a mixture of polypeptides from a protein sample; (b) separating the polypeptides by molecular weight; (c) contacting the separated polypeptides with a binding affinity reagent which binds specifically to a polypeptide containing a crotonyllysine residue; and (d) detecting presence of a binding complex between the affinity reagent and one or more of the polypeptides. An example of the binding agent is an antibody, which may be prepared from animal serums, or is a monoclonal antibody or single-chain variable fragment.

9 Claims, 15 Drawing Sheets

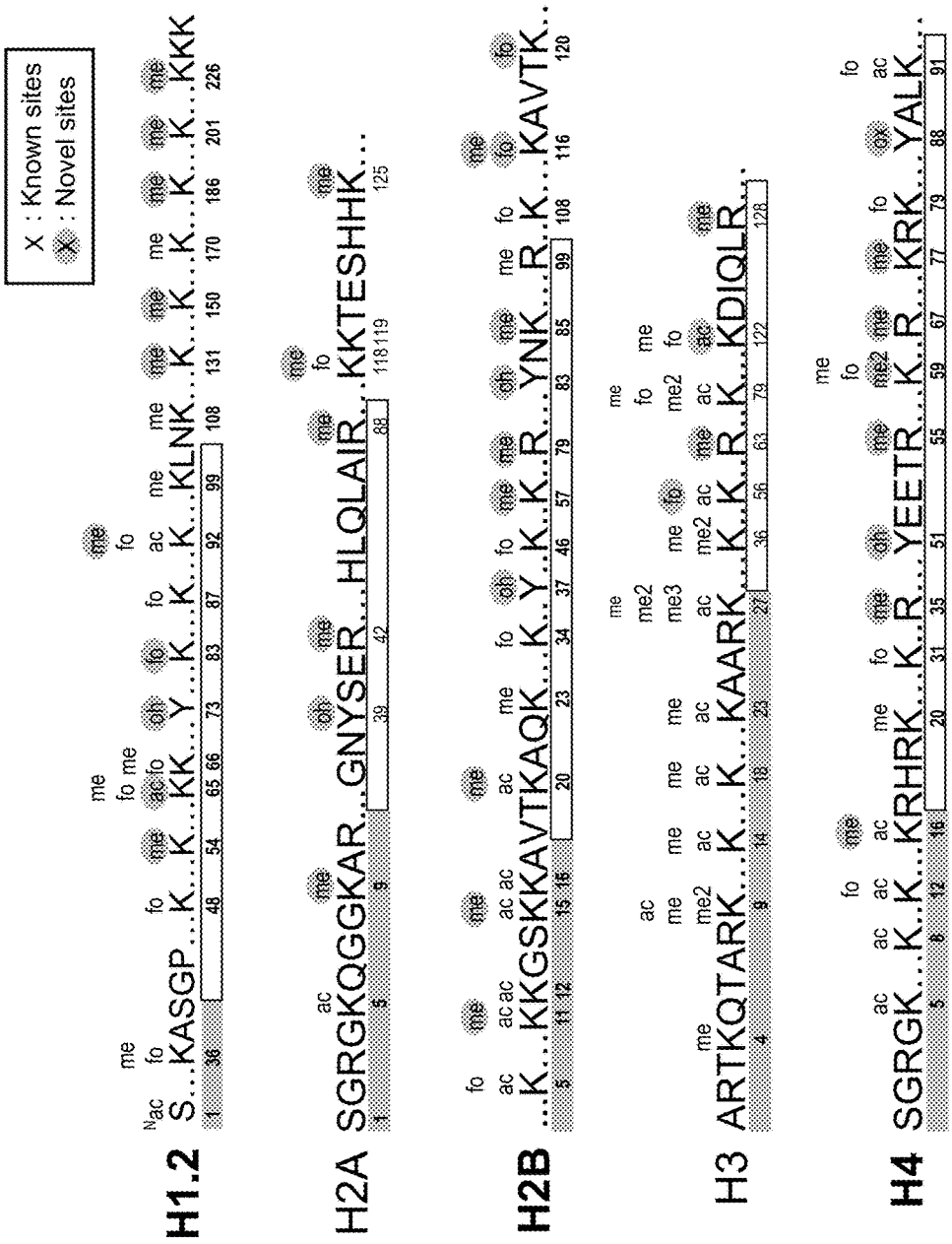
FIG. 1 (continue)

Kcr: lysine crotonylation   Kac: lysine acetylation

```
         Mouse:                                Kcr          Kcr
         Human:                         Kcr            KcrKcr     Kcr
H2A Human:  NH2-SGRGKQGGKARAKAKTR........LLRKGNY........AVLLPKKTESHHKAKGK-COOH
               5   9   13 15              36              118 119   125
               Kac Kac Kac Kac            Kac
```
SEQ ID No: 9

```
         Mouse:         Kcr    KcrKcr KcrKcr  Kcr Kcr    Kcr
         Human:         Kcr    KcrKcr KcrKcr  Kcr Kcr    Kcr
H2B Human:  NH2-PEPAKSAPAPKKGSKKAVTKAQKK.......RSRKESYSI........TKYTSSK-COOH
                 5      11 12  15 16  20 23 24   34
                 Kac    Kac   Kac    Kac  Kac
```
SEQ ID No:10

```
         Mouse:         Kcr  Kcr         Kcr  Kcr Kcr   Kcr
         Human:         Kcr  Kcr         Kcr  Kcr Kcr   Kcr
H3 Human:  NH2-ARTKQTARKSTGGKAPRKQLATKAARKS......RYQKST...RIRGERA-COOH
               4    9    14   18   23  27    56
               Kac  Kac  Kac  Kac  Kac Kac   Kac
```
SEQ ID No:11

```
         Mouse:         Kcr Kcr    Kcr
         Human:         Kcr Kcr  Kcr
H4 Human:  NH2-SGRGKGGKGLGKGGAKRHRKVLRDNIQG........TLYGFGG-COOH
                5   8  12  16  20
                Kac Kac Kac Kac Kac
```
SEQ ID No:12

```
           Mouse:             Kcr    Kcr   Kcr               Kcr   Kcr
           Human:             Kcr    Kcr   Kcr    Kcr   Kcr  Kcr   Kcr
H1.2 Human: NH2-SET..PRKASGP..ALKKAL..GLKSLVSKGTLVQTKG.....KAKK..ATVTKKVA........KK-COOH
                    33         63     84      89       96    158   167
```
SEQ ID No:13

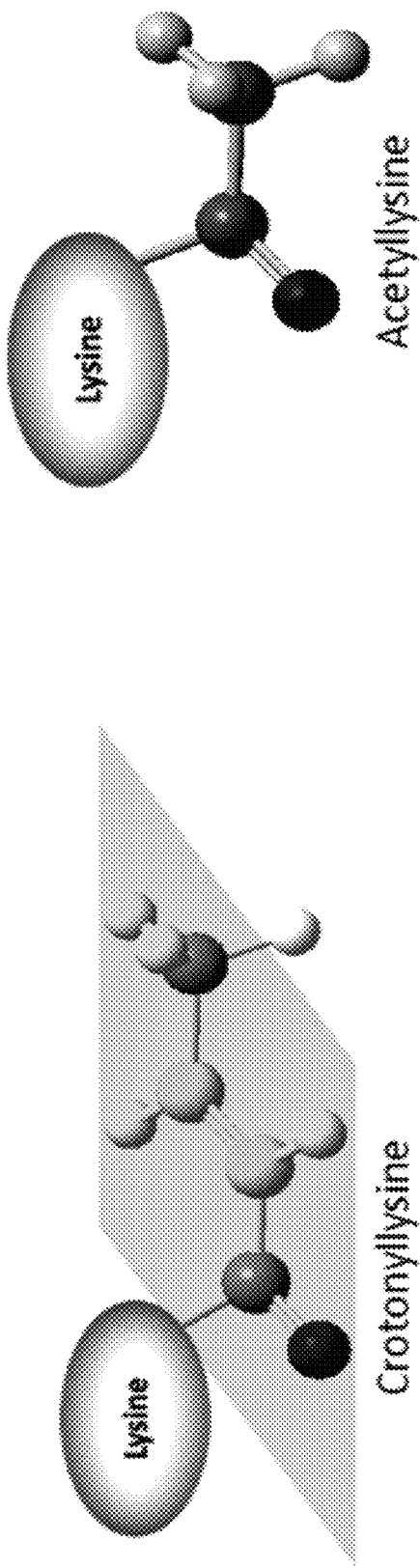
FIG. 2 (continue)
B

FIG. 2 (continue)
c
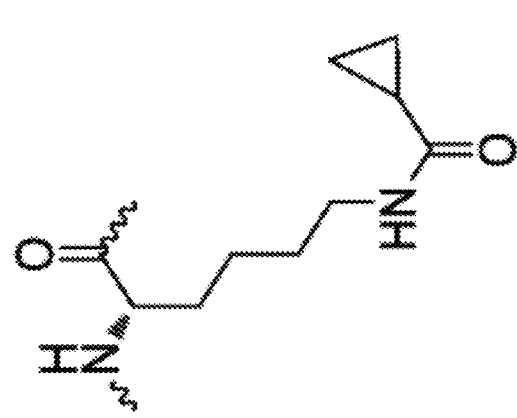
cyclopropanecarboxyllysine
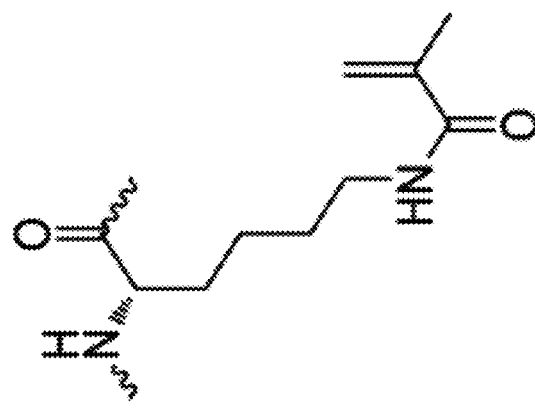
Methacryllysine
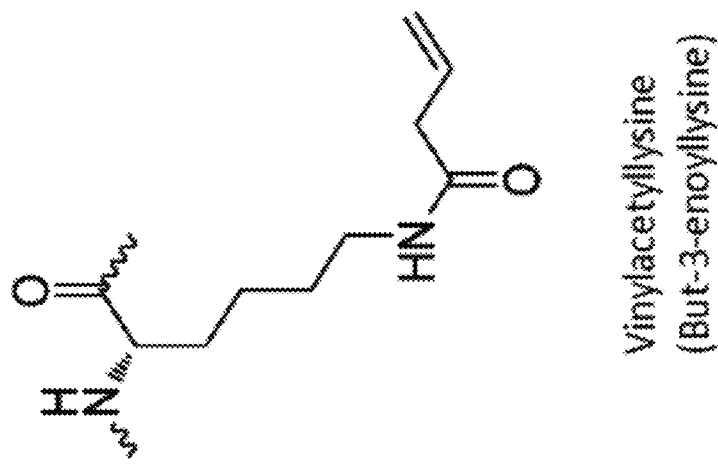
Vinylacetyllysine
(But-3-enoyllysine)

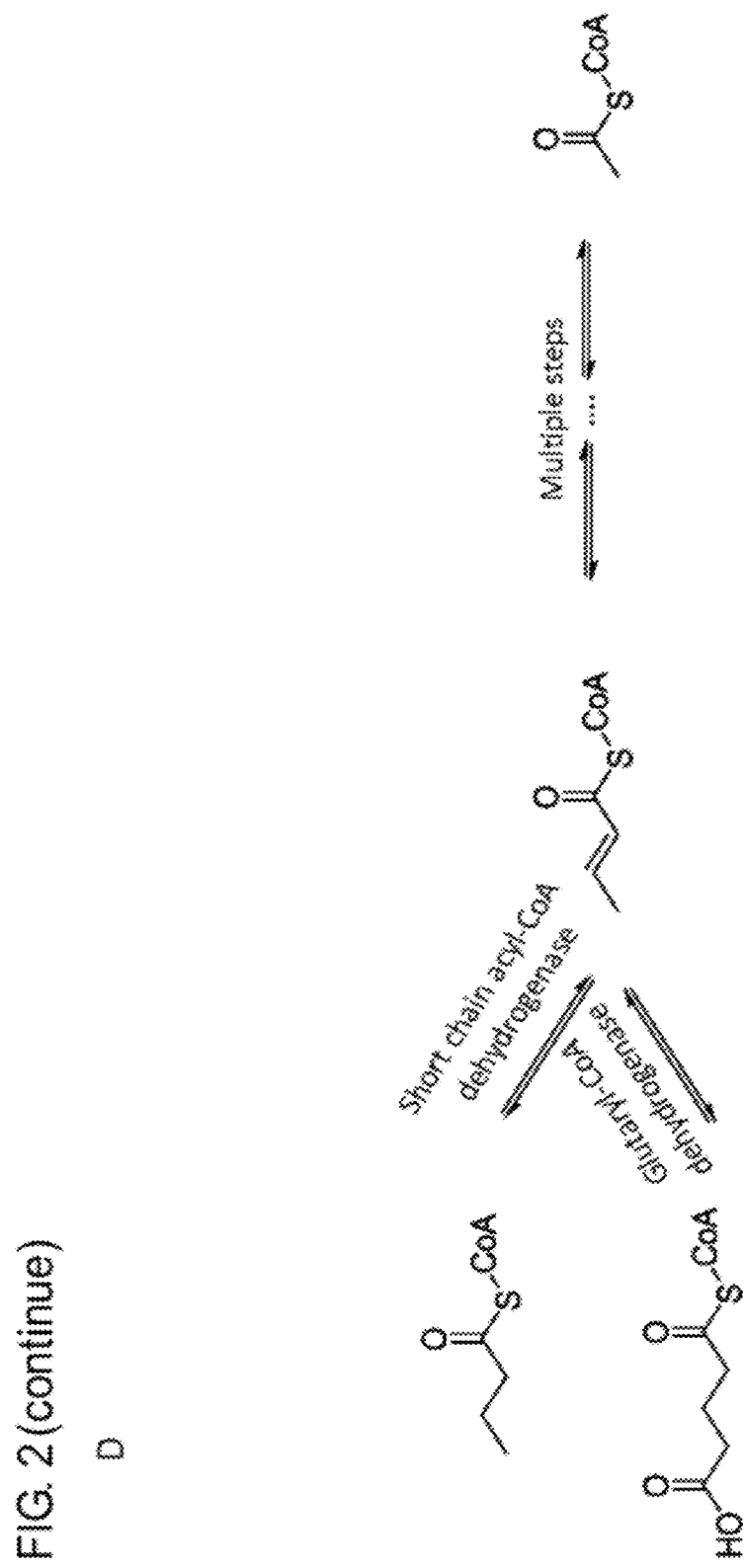
FIG. 2 (continue)
D

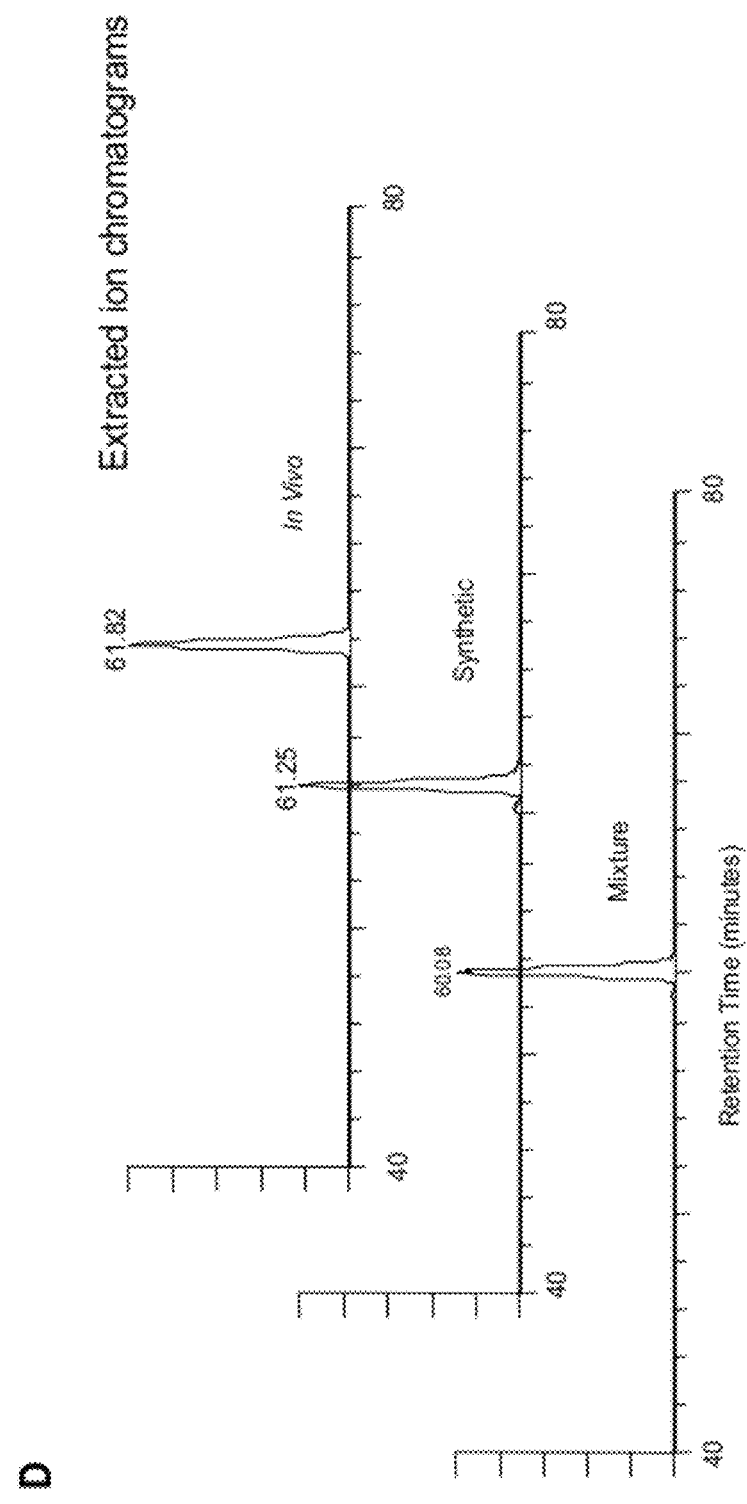
FIG. 3 (continue)

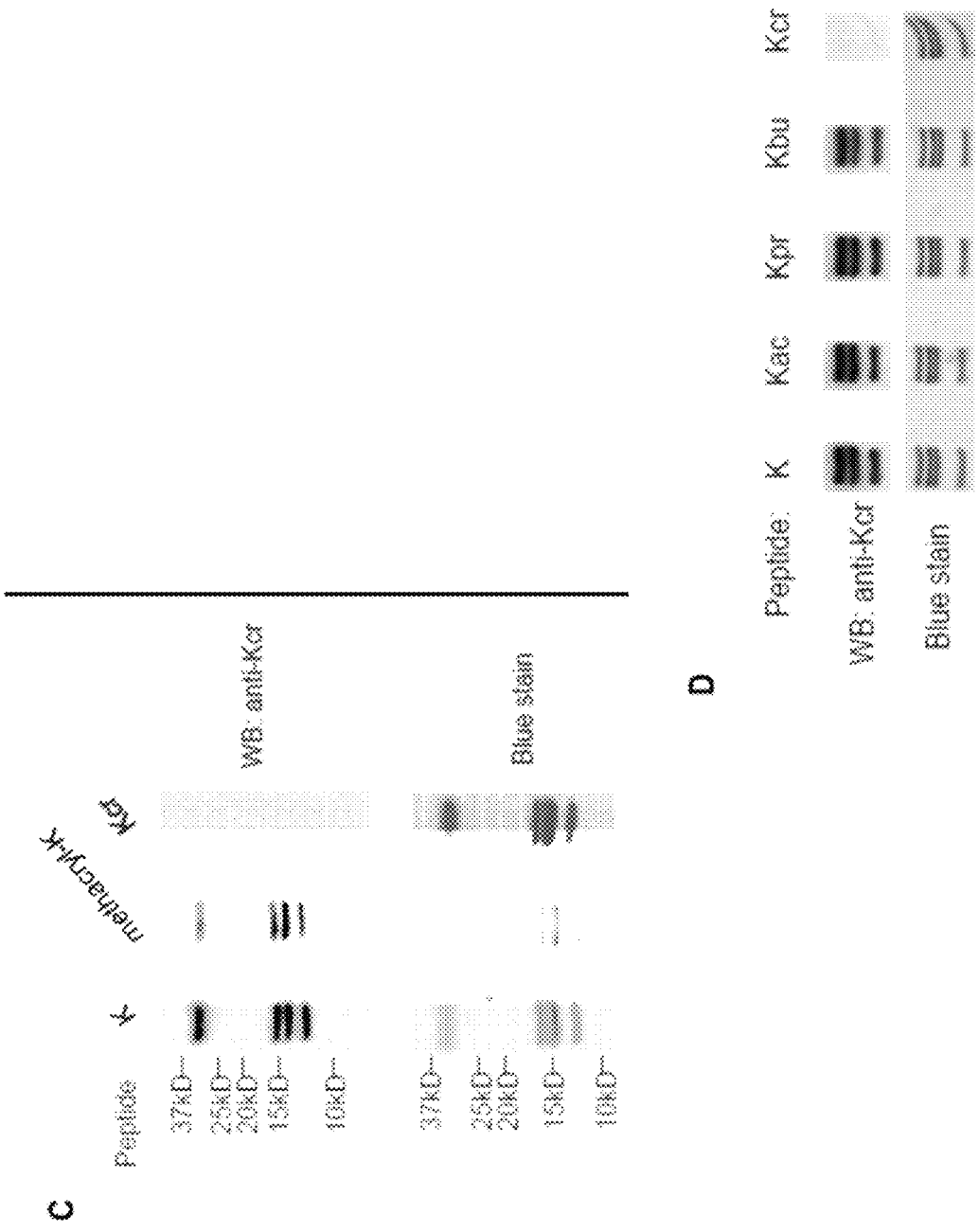
FIG. 4 (continue)

A

B

AGENT AND METHOD FOR IDENTIFYING LYSINE CROTONYLATION IN PROTEINS

CROSS REFERENCE TO RELATED APPLICATION

This invention claims benefit from U.S. Provisional Application No. 61/349,185, filed on May 27, 2010, the content of which is incorporated herewith by reference in its entirety.

FIELD OF THE INVENTION

This invention relates to a method and its related agent for detecting a post-translational modification of proteins in mammals. More particularly, it relates to a method and a protein affinity reagent for detecting lysine crotonylation of proteins as a form of post-translational modification (hereinafter PTM).

BACKGROUND OF THE INVENTION

Molecular anatomy of post-translational modifications that regulate cellular processes and disease progression stands as one of the major goals of post-genomic biological research. To date, more than 300 post-translational modifications have been described, which provide an efficient way to diversify a protein's primary structure and possibly its functions. The remarkable complexity of these molecular networks is exemplified by modifications at the side chain of lysine, one of the fifteen ribosomally-coded amino acid residues known to be modified. The electron-rich and nucleophilic nature of the lysine side chain makes it suitable for undergoing covalent post-translational modification reactions with diverse substrates that are electrophilic. The residue can be potentially modulated by several post-translational modifications including methylation, acetylation, biotinylation, ubiquitination, and sumoylation, which have pivotal roles in cell physiology and pathology.

Histones, for example, are known to be modified by an array of post-translational modifications, including methylation, acetylation, ubiquitination, small ubiquitin-like modification, and ribosylation. A combinatorial array of post-translational modifications in histones, termed the "histone code", dictates the proteins' functions in gene expression and chromatin dynamics. Post-translational modifications of histones have been studied by both biochemistry (Jenuwein, et al. 2001) and mass spectrometry (Garcia, et al. 2007; Boyne, et al. 2006; Medzihradszky, et al. 2004).

Lysine acetylation is an abundant, reversible, and highly regulated post-translational modification. While initially discovered in histones, the modification was later identified in non-histone proteins, such as p53. A recent proteomics screening showed that acetyllysine is abundant and present in substrates that are affiliated with multiple organelles and have diverse functions. Interestingly, the modification is enriched in mitochondrial proteins and metabolic enzymes, implying its roles in fine-tuning the organelle's functions and energy metabolism. The modification plays an important roles in diverse cellular processes, such as apoptosis, metabolism, transcription, and stress response. In addition to their roles in fundamental biology, lysine acetylation and its regulatory enzymes (acetyltransferases and deacetylases) are intimately linked to aging and several major diseases such as cancer, neurodegenerative disorders, and cardiovascular diseases.

SUMMARY OF THE INVENTION

An object of the present invention is to provide an agent for detection of post-translational modifications at the lysine residue. This object is achieved by providing a protein affinity reagent, preferably an antibody, which specifically binds a protein or polypeptide having a crotonyllysine residues, but does not substantially bind a protein or polypeptide that does not have a crotonyllysin residue. A protein "affinity reagent" as used in this invention is any protein or polypeptide that is capable of recognizing and binding with sufficient specificity to a particular type of proteins or polypeptides bearing a crotonyllysine. One example of such an affinity reagent is an antibody. As another example, an affinity reagent for detection of lysine crotonylation can be generated from screening of protein libraries, including but not being limited to phagy library, yeast library.

Another object of the present invention is to provide a method for detection of post-translational modifications at the lysine residue. This object is realized by a process that comprises the steps of (a) obtaining a sample comprising polypeptides; (b) separating the polypeptides according to their molecular weights; (c) contacting one or more of the separated polypeptides with a binding agent, such as an antibody, that specifically binds a polypeptide having a crotonyllysine, but does not substantially bind a polypeptide that does not have a crotonyllysine; and (d) detecting the binding of the binding agent to the polypeptides, whereby the binding of the binding agent to the polypeptides indicates the presence of the crotonyllysine in the polypeptides.

The sample used for practice the present invention may be obtained from a tissue biopsy or a clinical fluid from an organism in different conditions, such as, for example, in a diseased condition or under a therapeutic treatment. Similarly, reference samples may be obtained from an organism under normal healthy condition. When preparing the sample comprising polypeptides, an enzyme inhibitor may be preferably used to prevent undesired degradation. Examples of the enzyme inhibitor are aprotinin (Trasylol™), phenylmethylsulfonyl fluoride (PMSF), benzamidine, diisopropylfluorophosphate (DIFP), leupeptin, pepstatin, EDTA, EGTA. For separating the polypeptides, the sample may be heated to a temperature sufficient to denature the polypeptides without significantly degrading peptide bonds of the polypeptides. Before contacting with the binding agent specific to crotonyllysine, the separated polypeptides may be preferably immobilized on a solid support. The solid support may be built, for example, in a detecting kit. By a way of example, but not a limitation to the present invention, the detection of the presence of the binding complex between the binding agent (such as an antibody) and a protein or polypeptide containing one or more crotonylated lysine residues may be conducted by a Western blotting method. As it is understood by a person of ordinary skill in the art, the detection assay may include a negative control, positive control, or both.

As specific embodiments of the present invention, the isolated antibody as an example of the affinity reagent specific to the crotonylated lysine residue may be isolated from serums of immunized mammals, such as rabbits. It can also be monoclonal antibodies or in the form of single-chain variable fragments. Examples of the antibodies are antibody specific to histone H2A of which lysine 36, lysine 118, lysine 119, or lysine 125 is crotonylated; antibody to histone H2B of which lysine 5, lysine 11, lysine 12, lysine 15, lysine 16, lysine 20, lysine 23, or lysine 34 is crotonylated; antibody to H3 of which lysine 4, lysine 9, lysine 18, lysine 23, lysine 27, or lysine 56; antibody to histone H4 of which lysine 5, lysine-8, lysine 12, or lysine 16 is crotonylated; and antibody to histone H1 of which lysine 33, lysine 63, lysine 84, lysine 89, lysine 96, lysine 158, or lysine 167 is crotonylated. The above listed antibodies are provided as example, not as limitation to the present invention. By following the same or similar procedure as disclosed herewith or using other procedures known in the art, antibodies to other crotonylated proteins can be produced without undue experimentation by a person with ordinary skill in the art.

The various features of novelty which characterize the invention are pointed out with particularity in the claims annexed to and forming a part of this disclosure. For a better understanding of the invention, its operating advantages, and specific objects attained by its use, reference should be made to the drawings and the following description in which there are illustrated and described preferred embodiments of the invention.

DETAILED DESCRIPTION OF PARTICULAR EMBODIMENTS OF THE INVENTION

Materials

Figure 1:
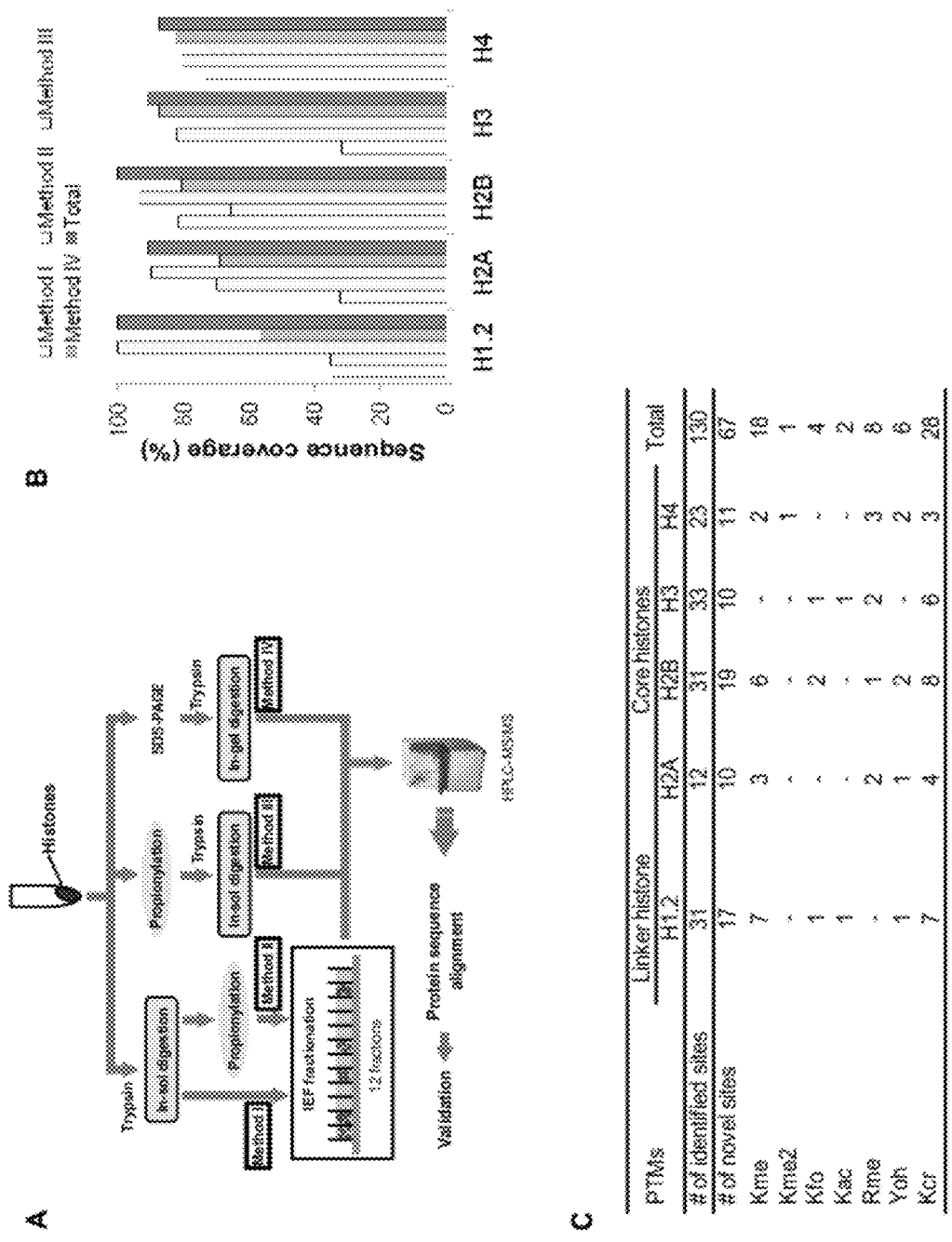
FIG. 1 summarizes the strategy and results for identifying histone PTM sites according the present invention.

All peptides used in this study were synthesized through customer synthesis using Fmoc-Lysine (crotonyl)-OH. All chemicals of the highest purity available or analytical grade and Flag M2 antibody were purchased from Sigma-Aldrich, Inc. (St. Louis, Mo.). HA antibody was purchased from Roche Diagnostics (Indianapolis, Ind.). The histones were extracted from *S. cerevisiae* cells, S2 cells, mouse embolic fibroblast (MEF) cells, human Caucasian fetal lung fibroblast (IMR90) cells, and HeLa cells using previously known procedures (Shechter et al., 2007; Tateishi et al., 2009). 4,4,4,3-D4-crotonic acid was prepared using D4-acetaldehyde (Cambridge Isotope Laboratories, Andover, Mass.) and malonic acid. Polyclonal pan anti-Kcr and anti-Kac antibodies were generated in house using a procedure described below.

Preparation of Histones from Hela Cells

The process of preparing HeLa cell histones were known (Zhang et al., 2010). HeLa cells were grown in DMEM culture medium supplemented with 10% fetal bovine serum. The cells were then harvested and washed twice with ice-cold PBS containing 5 mM sodium butyrate. The cells were lysed in TRITON® extraction buffer (TEB; PBS containing 0.5% (v/v) TRITON® X-100 (polyethylene glycol p-(1,1,3, 3-tetramethylbutyl)-phenyl ether), 2 mM PMSF, and 0.02% (w/v) NaN3). After centrifugation, the supernatant was removed. The pellet was washed, centrifuged, and resuspended in 0.4 N $H_2SO_4$ overnight at 4° C. After centrifugation, the supernatant was removed; histones in the supernatant were precipitated by the addition of 20% (v/v, final concentration) TCA to the protein solution. The suspension was incubated at −20° C. for 4 hrs. The protein precipitate was spun down, collected, and washed with acidified acetone (0.1% (v/v) HCL), followed by two washes with ice-cold acetone. After being dried at room temperature, the pellets were dissolved in water.

In-Solution Proteolytic Digestion and Chemical Derivatization of Histone Proteins In-solution tryptic digestion of histone samples was carried out using a known protocol (Kim et al., 2006; Luo et al., 2008). In vitro lysine propionylation of histone extract and tryptic histone peptides was performed as known in the art (Garcia et al., 2007a). Three different processes of proteolytic digestion were performed: histone extracts were (i) in-solution digested without chemical propionylation, (ii) chemically propionylated after in-solution digestion, or (iii) chemically propionylated before in-solution digestion.

Isoelectric Focusing (IEF) Fractionation

The histone proteolytic peptides were separated using an Agilent 3100 OFFGEL Fractionator (Agilent, Santa Clara, Calif.) according to the manufacturer's instructions and generally known in the art. Twelve fractions were obtained from each IEF fractionation experiment.

Synthesis of Bovine Serum Albumin (BSA) Derivatives

Five mg of but-3-enonylic acid, crotonic acid, or metharylic acid was mixed with 5 mg of BSA in 4 ml of PBS buffer, followed by the addition of 25 mg of 1-ethyl-3-(3-dimethylaminopropyl) carbodiimide (EDC). The mixture was stirred at room temperature for 4 hrs to generate vinylacetyl-BSA, crotonyl-BSA, and methacryl-BSA, respectively. The unreacted EDC and other small molecules were removed from BSA derivatives by gel filtration. The modified BSAs were confirmed by SDS-PAGE.

Conjugation of Crotonyllysine-Immobilized Agarose Beads

The crotonyllysine residue was conjugated to AminoLink Plus Coupling Resin (Pierce Biotechnology, Rockford, Ill.) following the manufacturer's protocol. Two mL of resin were washed with PBS and then suspended in 6 mL PBS. The beads were then mixed with 2 mg of the crotonylysine (pre-solubilized in 2 ml PBS) and then NaCNBH3 (to a final concentration of 50 mM) was added. After incubation for 6 hrs at room temperature with agitation, the beads were washed by 4 ml of PBS and then blocked by 2 ml of 1.0 M Tris.HCl, pH 7.4 for 30 min at room temperature. The beads were sequentially washed with 10 mL of 1.0 M NaCl and 4 ml of PBS.

Generation of Pan Anti-Crotonyllysine Antibodies

The anti-crotonyllysine IgG was developed by immunizing 10 rabbits with lysine-crotonylated BSA. The rabbits were immunized with four injections. Five batches of serums were collected from each rabbit. The serum with the highest ELSA titer was used for enriching anti-crotonyllysine antibody.

The pan anti-crotonyllysine antibody was enriched using the crotonyllysine-conjugate agarose beads. About 10 mL of serum were incubated overnight with 2 mL of the crotonyllysine-conjugated agarose beads in a column. The beads were then sequentially washed with 20 mL of PBSN buffer (PBS containing 0.5% NP40), 20 mL of PBSS buffer (PBS containing 0.1% SDS), 6 mL of PBSS (PBS containing 0.8 M NaCl), and 6 mL of PBS. The bound antibodies were eluted from the beads with 0.1 M glycine (pH 3.0) and immediately neutralized with 1.0 M Tris-HCl (pH 8.5). The antibodies were dialyzed against in cold PBS overnight. Both dot-spot assay and Western blotting were performed to check quality of the antibody.

The pan anti-Kac antibodies were developed likewise using lysine-acetylated BSA as an antigen. The antibody was purified using acetyllysine-conjugated agarose by the above procedure.

Figure 7:
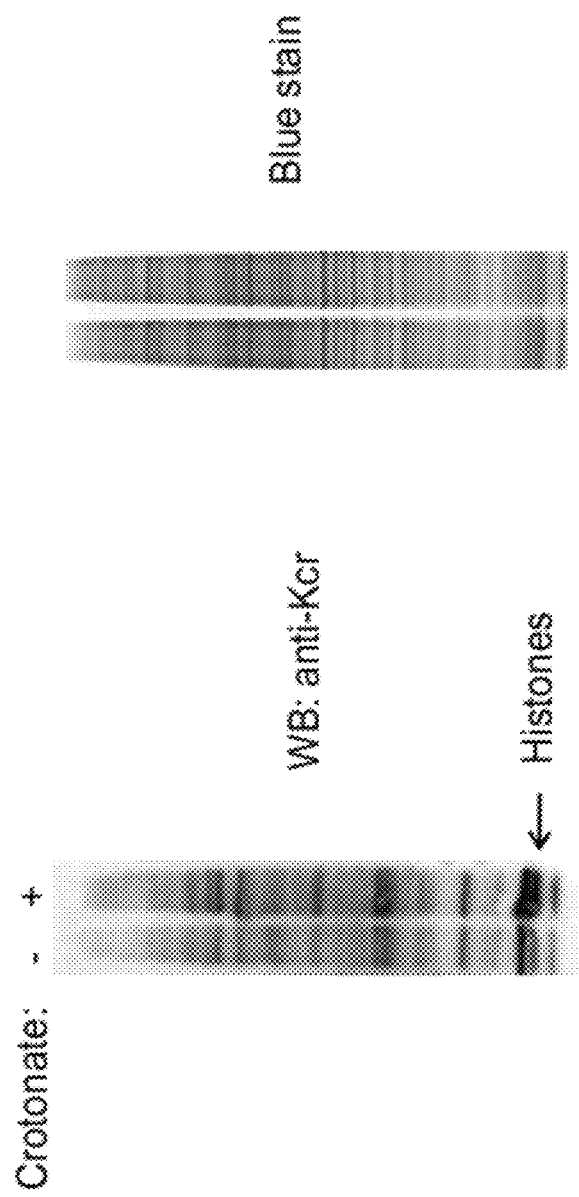
FIG. 7 shows the result of detection of lysine crotonylation in HeLa cell lysates with pan anti-Kcr antibody by Western blotting.

FIG. 7 is the Western blot result showing the existence of lysine crotonylation in HeLa cell lysates with pan anti-Kcr antibody. HeLa cells were cultured in DMEM medium with/without crotonate (50 mM) for 12 hrs. cells were lysed with sampling buffer. The protein from whole cell lysates were resolved on SDS-PAGE and Western blotting by anti-Kcr antibody.

Generation of Sequence-Specific Anti-Crotonyllysine Antibodies

As a particular embodiment, a sequence-specific anti-H3K23 crotonyllysine antibody was developed by immunizing rabbits with an antigen peptide bearing a crotonyllysine residue, CQLATKAA (SEQ ID No:1), where C is a cystein residue, and the underlined K indicates crotonyllysine residue. The rabbits were immunized with four injections. Five batches of serums were collected from each rabbit. The serum with the highest ELSA titer was used for enriching sequence-specific anti-crotonyllysine antibodies antibody.

The sequence-specific anti-crotonyllysine antibodies was enriched using the antigen-conjugated agarose beads. The serums were centrifuged at 20,000 g to remove possible protein particles. About 10 mL of serum were incubated overnight with 2 mL of the crotonyllysine-containing peptide antigen conjugated agarose beads in a column. The beads were then sequentially washed with 20 mL of PBSN buffer (PBS containing 0.5% NP40), and 6 mL of PBS. The bound antibodies were eluted from the beads with 0.1 M glycine (pH 3.0) and immediately neutralized with 1.0 M Tris-HCl (pH 8.5). The antibodies were dialyzed against in cold PBS overnight. The obtained antibodies were depleted by incubating with the agarose conjugated with a peptide, CQLATKAA (SEQ ID No:1), which has the same peptide sequence as the antigen peptide, but the lysine residue is not crotonylated. As it would be understood by a person with ordinary skill in the art, other antigen peptides other than the one used in this particular embodiment, i.e., CQLATEAA (SEQ ID No:1), may also be used to obtain satisfactory results. The design of the antigen peptide is based on the sequence around a lysine in the protein whose crotonylation is intended as the target of detection and requires only ordinary kill in the art.

With the same method, another antigen peptide CYQ KSTELL (SEQ ID: No:2) (the underlined K is a lysine crotontylated), was used to generate sequence specific antibodies for H3K56 lysine crotonylation. The processes are the same as described in the above except that an different antigen peptide (i.e., CYQKSTELL)(SEQ ID: No:2) was used for targeting H3K56, that is, lysine crotonylation at position 56 of the H3 protein.

Figure 8:
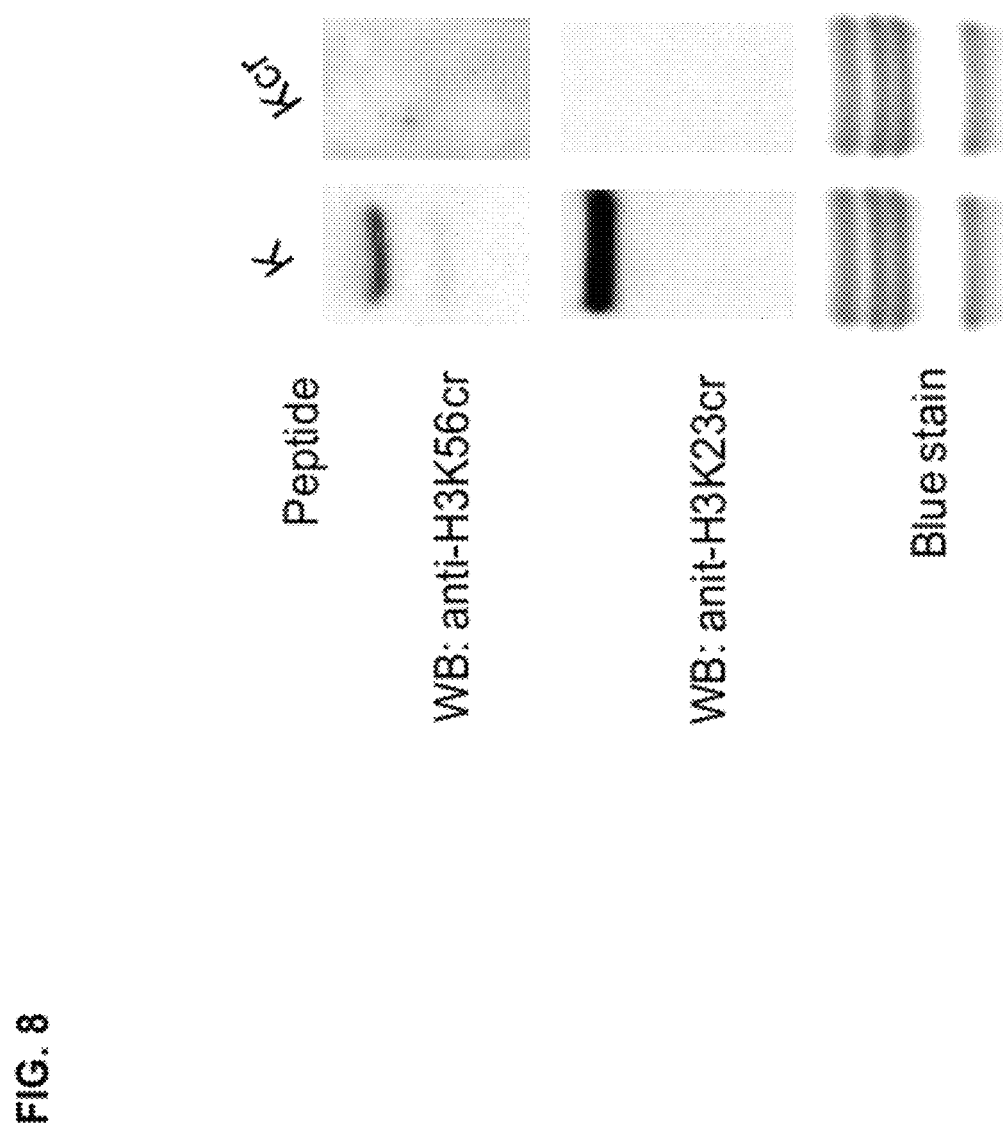
FIG. 8 shows the result of detection of H3K23 and H3K56 crotonylation by Western blotting using sequence-specific antibodies.

FIG. 8 shows the detection of H3K23 and H3K56 crotonylation by Western blotting using sequence-specific antibodies. Human HeLa histones were separated by SDS-PAGE and Western blotted by H3K23 or H3K56 crotonyllysine site specific antibody competed by nonmodified (K) or crotonyllysine (Kcr) sequence specific peptide.

While in the above embodiments anti-crotonyllysine IgG was used, people with ordinary skill of the art may practice the present invention with corresponding monoclonal antibodies or single-chain variable fragments (scFvs) to obtain a satisfactory result.

Affinity Enrichment of Crotonyllysine Peptides Using Anti-Kcr Antibody

The affinity-purified anti-crotonyllysine antibody was immobilized to protein A agarose beads (GE Healthcare Biosciences, Pittsburgh, Pa.) by incubation at 4° C. for 4 hrs. The supernatant was removed and the beads were washed three times with NETN buffer (50 mM Tris.HCl [pH 8.0], 100 mM NaCl, 1 mM EDTA, 0.5% NP40). The histone tryptic peptides were resolubilized in NETN buffer. Affinity purification was carried out by incubating the peptides with 20 µl of anti-crotonyllysine antibody-immobilized protein A beads at 4° C. overnight with gentle shaking. The beads were washed three times with NETN buffer and twice with ETN buffer (50 mM Tris.HCl pH 8.0, 100 mM NaCl, 1 mM EDTA). The bound peptides were eluted from the beads by washing three times with 50 µl of 0.1% TFA. The elutes were combined and dried in a SpeedVac.

Western Blotting with Competition with a Peptide Library

One µg of histone protein extracts were resolved in SDS-PAGE. Crotonylation signal was detected by pan anti-crotonyllysine antibody with competition by a peptide library bearing a non-modified, acetyl, propionyl, butyryl, methacrylyl, or crotonyl lysine.

In-Solution Proteolytic Digestion and Chemical Derivatization of Histone Proteins Histone tryptic peptides were generated by three methods: (i) Generation of histone peptides without in-vitro lysine propionylation. The histone pellet obtained above was suspended in 50 mM ammonium bicarbonate solution (pH 8.4) and was digested using a protocol previously described (Kim et al., 2006; Luo et al., 2008). (ii) In vitro lysine propionylation after histone tryptic digestion. The in vitro chemical reaction was performed as previously described (Garcia et al., 2007b). To generate derivatized histone peptides, 3 mg of histone tryptic digests obtained above were dissolved in 25 µl of 100 mM ammonium bicarbonate buffer (pH 8.0), and 600 µl of 50% propionic anhydride in methanol (v/v) was added into the solution. The pH of the solution was quickly adjusted to pH 8.0 with ammonium hydroxide. The mixture was then incubated at 51° C. for 20 min and dried in a SpeedVac. The procedure was repeated once to ensure completion of the chemical reaction. (iii) In vitro lysine propionylation of core histones prior to tryptic digestion. Histones were derivatized by propionylation reaction as described above, and the derivatized histones were subjected to in-solution tryptic digestion overnight.

HPLC/MS/MS Analysis and Protein Sequence Database Searching

The dried peptide extracts were dissolved in 3 µl HPLC solvent A (0.1% formic acid in water, v/v). 1 µl sample was injected into a NanoLC-1D plus HPLC system (Eksigent Technologies, Dublin, Calif.), which was connected to a home-made capillary Jupiter C12 column (10 cm length×75 µm ID, 4 µm particle size, 90 Å pore size; Phenomenex, St. Torrance, Calif.). Peptides were eluted with a 2-hour gradient of 2% to 80% HPLC solvent B (0.1% formic acid in acetonitrile, v/v) in solvent A at a flow rate of 200 nl/min. Peptides were then ionized and analyzed by LTQ Orbitrap Velos mass spectrometer (ThermoFisher Scientific, San Jose, Calif.) using a nano-spray source. High-resolution full scan MS spectra (from m/z 350-1400) were acquired in the Orbitrap with resolution R=60,000 at m/z 400 and lockmass enabled (m/z at 445.120025), followed by MS/MS fragmentation of the twenty most intense ions in the linear ion trap with collisionally activated dissociation (CAD) energy of 35%. The exclusion duration for the data-dependant scan was 36 seconds, and the exclusion window was set at ±0.01% m/z.

The MS/MS data were analyzed by both non-restrictive sequence alignment by PTMap algorithm (Chen et al., 2009) and sequence alignment using limited, pre-specified PTMs by Mascot algorithm. The specific parameters for protein sequence database searching included lysine mono-, di- and tri-methylation, formylation and acetylation, arginine mono-methylation and di-methylation, tyrosine hydroxylation, methionine oxidation, and lysine crotonylation (K+68.02621 Da) as variable modifications for non-propionylated histones. For histone samples generated by tryptic digestion of propionylated histones, the specific parameters included lysine propionylmethylation (+70.04187 Da) and lysine propionylation as variable modifications. For histone samples propionylated after trypsin digestion, N-terminal propionylation was included as a fixed modification. Other parameters used in data analysis were: six allowed missing cleavages; mass error of 10 ppm for precursor ions, and 0.6 Da for fragment ions. Charge states of +1, +2, and +3 were considered for parent ions. If more than one spectrum was assigned to a peptide, only the spectrum with the highest Mascot or PTMap score was selected for manual analysis. All peptides identified with peptide scores of PTMap>0.8 and Mascot>20 were manually examined using rules known in the art (Chen et al., 2005).

Verification of Lysine Crotonylated Peptides by HPLC/MS/MS Analysis

The lysine crotonylated peptide in tryptic digest of histones, its synthetic counterpart, and their mixture were injected into nano-HPLC system and analyzed by high-resolution MS and MS/MS in the Orbitrap mass spectrometer, respectively. Full MS scans were acquired with resolution R=30,000 at m/z 400 with lockmass enabled (m/z at 445.120025), and targeted MS/MS spectra were acquired at a resolution of 7,500 at m/z 400.

Identification of Kcr Peptides

Histone proteins have a high ratio of both lysine and arginine residues. Thus, many histone tryptic peptides are relatively small and hydrophilic, some of which cannot be retained in a C18 RP-HPLC column for subsequent detection by MS. This problem can be addressed by chemical derivatization (e.g., lysine propionylation) of amine groups in the protein (N-terminal amines, and free and monomethylated lysine $\epsilon$-amino groups) before or after tryptic digestion. Similarly, lysine propionylation of core histones, before or after tryptic digestion, will generate complementary peptide sequences that boost the sequence coverage of peptide mapping by MS. Additionally, IEF separation of tryptic digest into 12 fractions will further reduce peptide complexity and improve dynamic range.

In the present invention, as a particular embodiment, the integrated approach was designed for systematic analysis of histone PTMs (i.e., post-translational modifications). The strategy and results for identifying histone PTM sites are shown in FIG. 1, which represented an effort to maximize both the sequence coverage and sensitivity, and to identify novel PTM sites. In this invention, MS analysis was carried out in histone proteolytic peptides that were generated by four parallel methods (see FIG. 1A): Histone extracts were in-solution tryptic digestion without chemical propionylation (Method I), chemically propionylated after in-solution tryptic digestion (Method II), chemically propionylated before in-solution tryptic digestion (Method III), and in-gel digested after SDS-PAGE gel separation. Samples from Methods I and II were further subjected to IEF fractionation to generate 12 fractions. FIG. 1B shows peptide sequence coverage of linker and core histones detected by the four methods. The PTM sites identified in the work as a particular embodiment of the invention are summarized in FIG. 1C, where abbreviations are "me" for monomethylation; "me2" for dimethylation; "me3" for trimethylation; "fo" for formylation; "ac" for acetylation; "oh" for hydroxylation; and "cr" for crotonylation.

PTMap, an algorithm capable of identifying all possible PTMs of a protein (Chen et al., 2009), was used to analyze all the acquired MS/MS data to identify histone peptides with or without a PTM. As anticipated, sequence coverage by MS mapping was significantly improved after in vitro propionylation, either before or after tryptic digestion (see FIG. 1B). Among the four methods, Method III (in vitro propionylation before tryptic digestion of histones) achieved the highest sequence coverage of histones H1.2 (100%), H2A (90.7%) and H2B (94.4%). Method IV gave the best coverage for histones H3 (87.3%) and H4 (82.3%). In aggregate, we achieved sequence coverage of 100% of H1.2, 90.7% of H2A, 100% of H2B, 91% of H3, and 87.3% of H4. To our knowledge, this represents the highest reported sequence coverage for peptide mapping in histones.

Using this approach, 130 unique PTM sites, including 28 Kcr sites (crotonylated lysine residue) were identified in the present invention. The remaining 102 non-Kcr modifications consist of 39 novel PTM sites, including 18 lysine monomethylation (Kme) sites, 1 lysine dimethylation (Kme2) site, 4 lysine formylation (Kfo) sites, 2 lysine acetylation (Kac) sites, 8 arginine monomethylation (Rme) sites and 6 tyrosine hydroxylation (Yoh) sites (see FIG. 1C).

A summary of the non-Kcr modification sites and Kcr sites identified in this study are shown in FIGS. 1D and 1E (where Kcr sites are underlined), respectively. All the MS/MS spectra for the identified histone PTM peptides were carefully verified as previously reported (Chen et al., 2005). It is confirmed the identification of Kcr peptides and 10 novel non-Kcr PTM sites by MS/MS of their corresponding synthetic peptides or by high-resolution MS/MS.

Identification of Kcr Residues in Histones

A PTM will induce structural and compositional changes in the substrate residue and therefore a change of its molecular weight. In the present invention, the analysis identified, on 28 lysine residues of the core histone peptides, a mass shift of +68 Da, which does not match the shift associated with any known PTM (see FIG. 1E), indicating a possible histone mark unknown previously.

Figure 2:
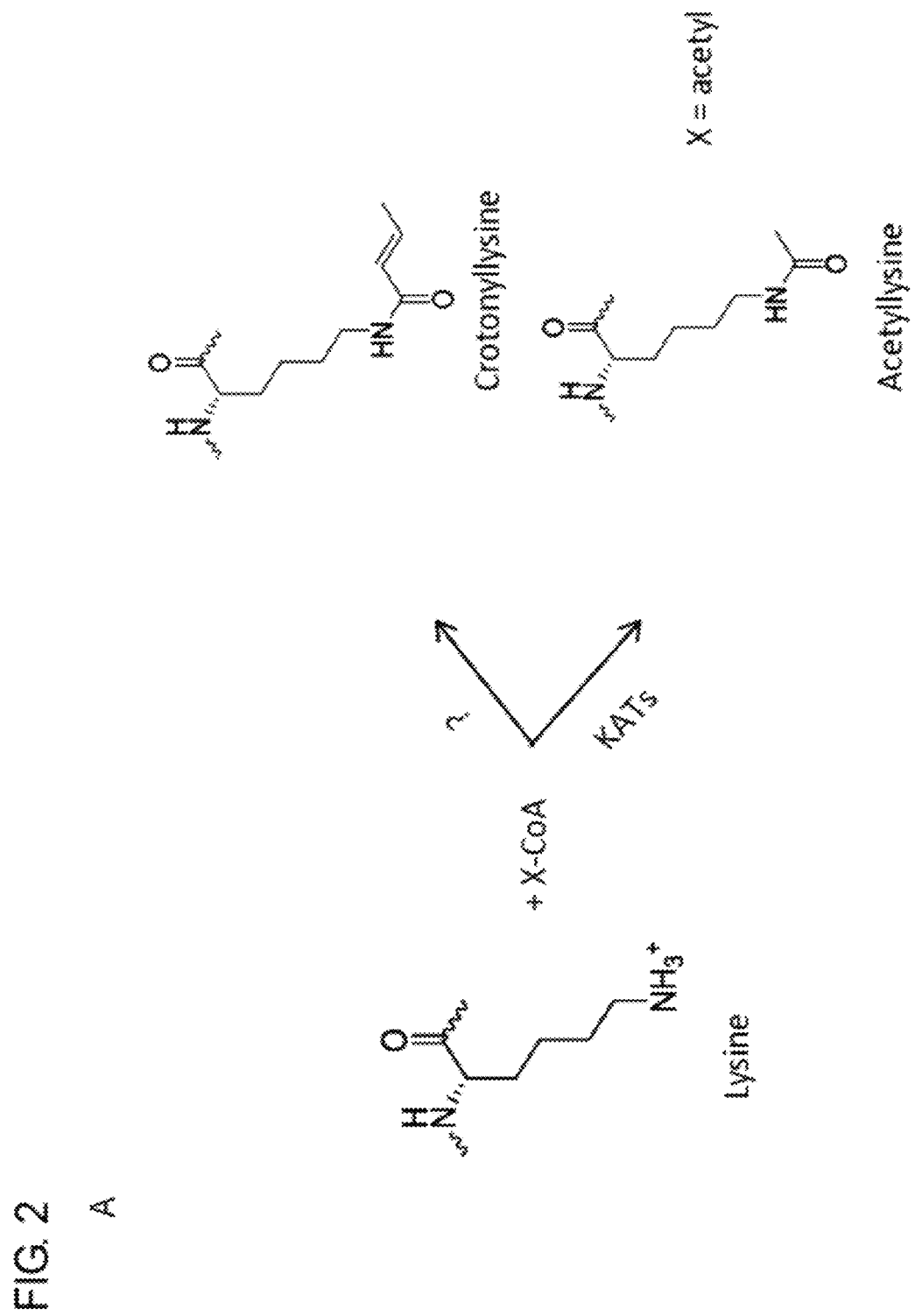
FIG. 2 shows two types of short-chain lysine acylations, resulting in crotonyllysine and acetyllysine, respectively.

To reveal the structure of this modification, one of these peptides, PEPAK+68SAPAPK (modified at H2BK5), was selected for further analysis. After manual inspection of the high-resolution MS data (precursor ion mass at m/z 580.8181) of this peptide, we determined the accurate mass shift of this modification as +68.0230 Da. By setting the mass tolerance to ±0.01 Da (~9 ppm, which is within the mass accuracy of the mass spectrometer used), and specifying a maximum of 2 nitrogen atoms, it was deduced, based on the mass shift, that the possible element compositions of the modification group as either $C_4H_4O$ or $H_6NO_3$. The former, $C_4H_5O$ (mass shift plus one proton), is the only reasonable molecular formula of this modification. There were 4 possible structures consistent with the element composition: Kcr (FIGS. 2A and 2B), vinylacetyllysine (3-butenoyllysine), methacryllysine, and cyclopropanecarboxyllysine (FIG. 2C). As crotonyl-CoA is an important and abundant intermediate (FIG. 2D), in metabolic pathways of butyryl-CoA and acetyl-CoA, Kcr was considered as a putative PTM candidate. FIG. 2A shows the chemical structures and an illustration of the enzymatic reactions for lysine acetylation by lysine acetyltransferases (KATs) using acetyl-CoA as a cofactor and the hypothesized mechanism for Kcr using crotonyl-CoA as a cofactor. In FIG. 2B, the ball-and-stick models of a crotonyl group and an acetyl group are shown. The three-dimensional arrangement of four carbons and one oxygen of the crotonyl group that are rigid and is located in the same plane (left). The two olefinic carbons of the crotonyl group are shown in the middle. In contrast, the tetrahedral $CH_3$ in the acetyl group (right) can be rotated that is structurally very different from the crotonyl group.

MS/MS of Synthetic Peptides and HPLC Coelution

Figure 3:
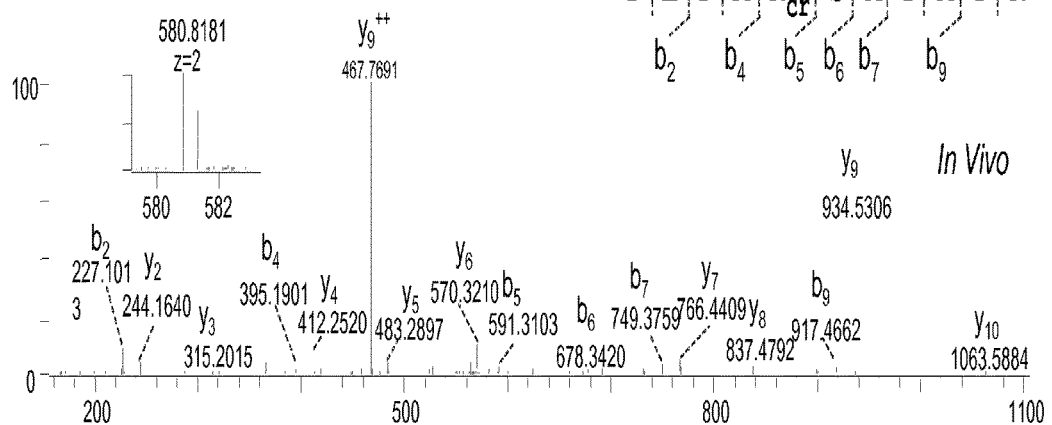
FIG. 3 shows the result of identification and verification of a Kcr peptide, PEPAKcrSAPAPK (SEQ ID: No: 3), where "Kcr" represents a crotonyllysine residue.
Figure 3:
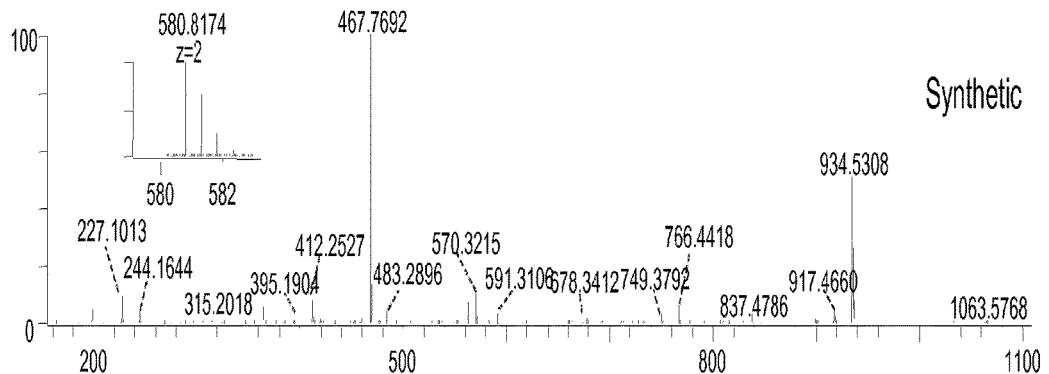
Figure 3:
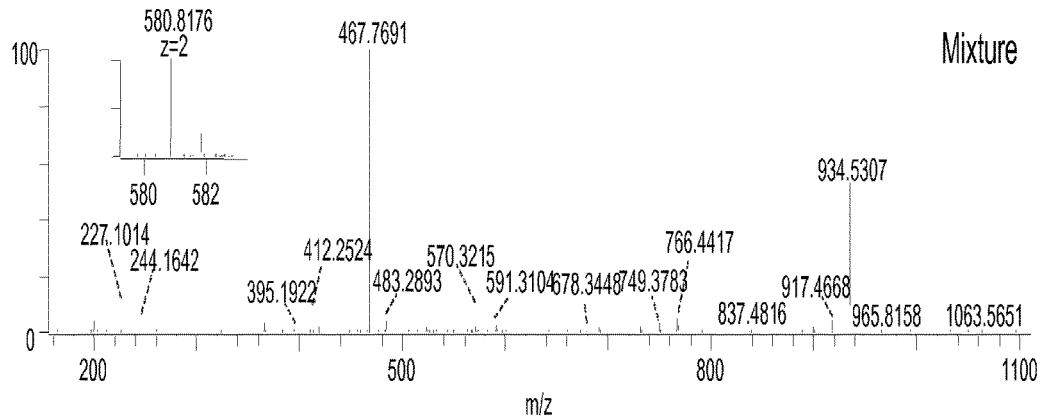

To test if the identified mass shift of +68.0230 Da was caused by Kcr, we synthesized the Kcr peptide, PEPAKcrSAPAPK (SEQ ID: No: 3), and compared its MS/MS spectrum with that of the in vivo-derived peptide. The in vivo modified peptide bearing a lysine residue with a mass shift of +68.0230 Da, the synthetic Kcr peptide with the same peptide sequence (PEPAKcrSAPAPK) (SEQ ID: No:3), and the mixture of the two peptides exhibited almost identical parent masses and high-resolution MS/MS spectra (FIGS. 3A to 3C). In addition, the mixture of the in vivo and synthetic peptides coeluted in HPLC/MS analysis (FIG. 3D). These results indicated that the identified mass shift of +68.0230 Da was very likely caused by Kcr.

Confirmation of Kcr Proteins by Western Blotting and Immunostaining

Figure 4:
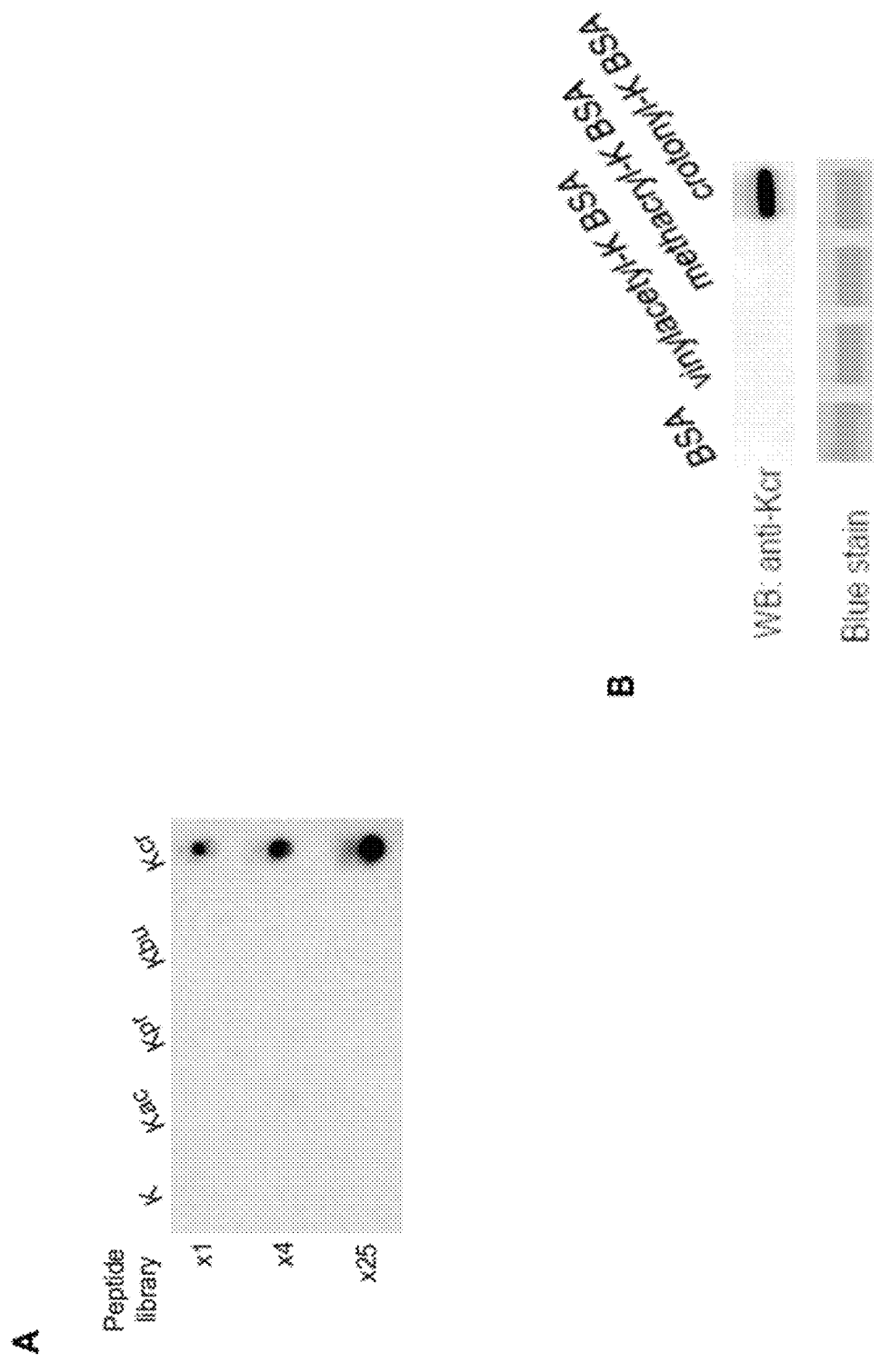
FIG. 4 shows the result of detection of Kcr in histones by Western blotting.

To further confirm Kcr in histones, a pan antibody was generated against Kcr. This pan anti-Kcr antibody specifically recognized a peptide library bearing Kcr, but not four other peptide libraries in which the fixed lysine residue was unmodified (K), ace tylated (Kac), propionylated (Kpr), or butyrylated (Kbu) (FIG. 4A). The specificity of the pan anti-Kcr antibody was also shown by Western blotting with three bovine serum albumin (BSA) derivatives, whose lysines were chemically modified by a crotonyl, vinylacetyl or methacryl group, respectively. The result showed that pan anti-Kcr antibody only recognized the lysine crotonylated BSA, but not the unmodified, lysine vinylacetylated or lysine methacrylated BSA (FIG. 4B). This pan anti-Kcr antibody was used for Western blotting and immunostaining of Kcr signal.

The antibody could detect a Kcr signal among all core histone proteins, H2A, H2B, H3, H4, and linker histone H1. In each protein, the signal could be efficiently competed away by a peptide library bearing a Kcr, but not the peptide library bearing an unmodified lysine (FIG. 4C), metharcryllysine (FIG. 4C), ace tyllysine, propionyllysine, or butyryllysine (FIG. 4D).

By independent confirmation based on five different methods, MS/MS and HPLC coelution of synthetic peptides, D4-crotonate labeling, Western blotting, and immunostaining, the present invention conclusively verified the existence of histone Kcr.

Confirmation of Kcr Proteins by In Vivo D4-Crotonate Isotopic Labeling

Figure 5:
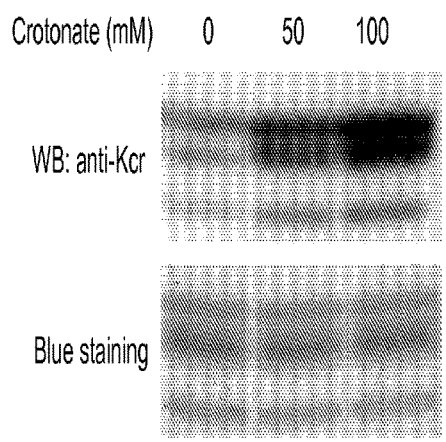
FIG. 5 shows the result of confirmation of Kcr proteins by in vivo D4-crotonate isotopic labeling.
Figure 5:
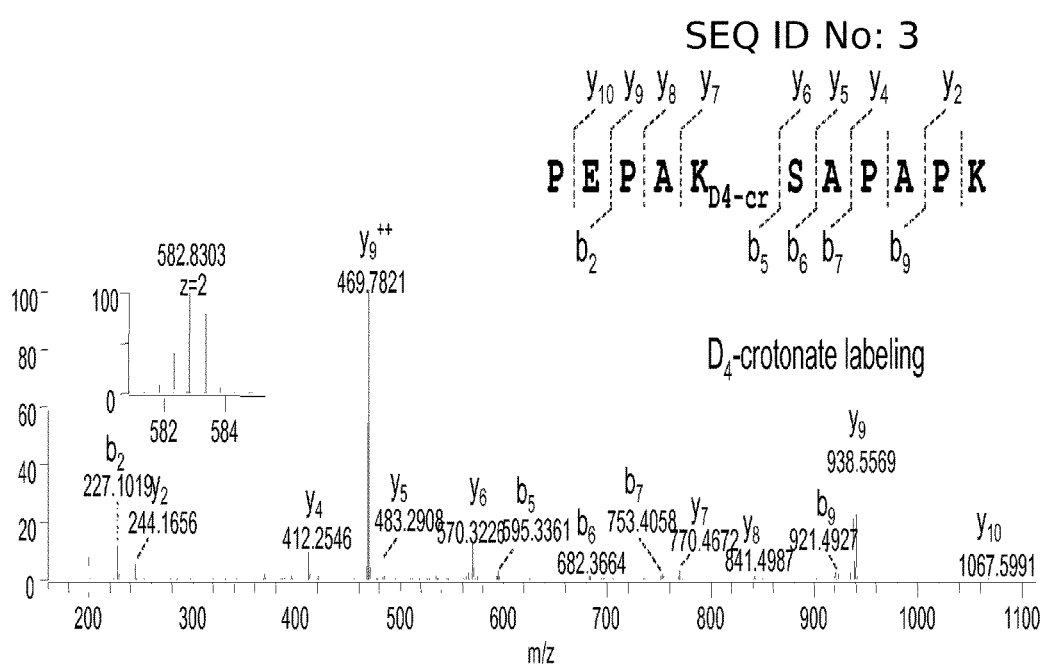

FIG. 5A shows the dynamics of histone Kcr in response to crotonate. The histone proteins extracted from human prostate cancer cell line Du145 incubated with 0, 50 or 100 mM crotonate for 24 hrs, were Western blotted with anti-Kcr pan antibody. FIG. 5B shows MS/MS spectrum of PEPA KD4-crSAPAPK identified from D4-crotonate-labeled sample. The mixture of D4-, D3- and D2-crotonyl groups was used for the identification of D4-crotonyl peptide.

Detection of Histone Kcr as in Different Cell Types

Figure 6:
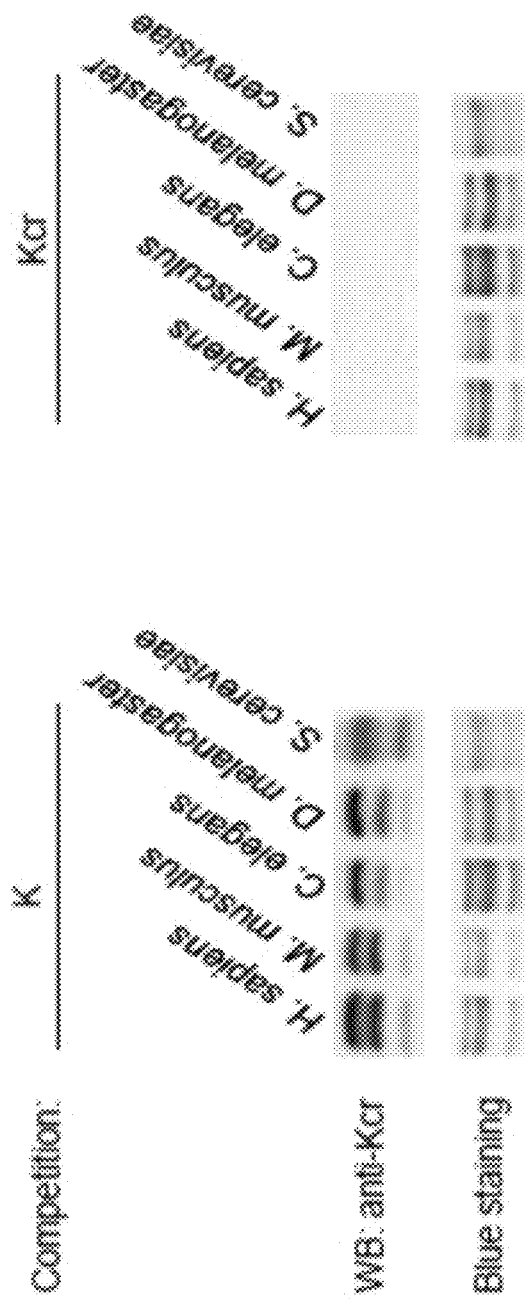
FIG. 6 shows the existence of Histone Kcr detected in different cell types.

Using the method of the present invention, it is further verified that lysine crotonylation is present in histones from other eukaryotic cells. For example, Kcr signals were detected among core histones in samples from yeast S. cerevisiae, Drosophila S2 cells, mouse embryonic fibroblast (MEF) cells, as well as human HeLa cells (FIG. 6). Taking advantage of affinity enrichment using the pan anti-Kcr antibody and HPLC/MS/MS, 24 Kcr sites were identified on mouse MEF cells. The results, therefore, revealed that Kcr is an evolutionarily conserved histone mark in eukaryotic cells.

The present invention provides an integrated approach for the systematic analysis of histone PTMs. With this unique approach, 130 PTM sites on human histones, including 63 known and 67 novel histone marks were identified as a particular embodiment of the invention, in which Yoh and Kcr were identified as two novel types of histone PTM. Therefore, the present invention has extended the catalogue of histone PTM sites in mammalian cells and provides a platform for the discovery of novel mechanisms of histone regulation and new ways of treating diseases related to histone regulation.

While there have been described and pointed out fundamental novel features of the invention as applied to a preferred embodiment thereof, it will be understood that various omissions and substitutions and changes, in the form and details of the embodiments illustrated, may be made by those skilled in the art without departing from the spirit of the invention. The invention is not limited by the embodiments described above which are presented as examples only but can be modified in various ways within the scope of protection defined by the appended patent claims.

REFERENCES

Chen, Y., Chen, W., Cobb, M. H., and Zhao, Y. (2009). PTMap—a sequence alignment software for unrestricted, accurate, and full-spectrum identification of post-translational modification sites. Proc Natl Acad Sci USA 106, 761-766.

Chen, Y., Kwon, S. W., Kim, S. C., and Zhao, Y. (2005). Integrated approach for manual evaluation of peptides identified by searching protein sequence databases with tandem mass spectra. J Proteome Res 4, 998-1005.

Chu, F., Nusinow, D. A., Chalkley, R. J., Plath, K., Panning, B., and Burlingame, A. L. (2006). Mapping post-translational modifications of the histone variant MacroH2A1 using tandem mass spectrometry. Mol Cell Proteomics 5, 194-203.

Cosgrove, M. S., Boeke, J. D., and Wolberger, C. (2004). Regulated nucleosome mobility and the histone code. Nat Struct Mol Biol 11, 1037-1043.

Garcia, B. A., Mollah, S., Ueberheide, B. M., Busby, S. A., Muratore, T. L., Shabanowitz, J., and Hunt, D. F. (2007a). Chemical derivatization of histones for facilitated analysis by mass spectrometry. Nat Protoc 2, 933-938.

Garcia, B. A., Pesavento, J. J., Mizzen, C. A., and Kelleher, N. L. (2007b). Pervasive combinatorial modification of histone H3 in human cells. Nat Methods 4, 487-489.

Garcia, B. A., Shabanowitz, J., and Hunt, D. F. (2007c). Characterization of histones and their post-translational modifications by mass spectrometry. Curr Opin Chem Biol 11, 66-73.

Johnson, L., Mollah, S., Garcia, B. A., Muratore, T. L., Shabanowitz, J., Hunt, D. F., and Jacobsen, S. E. (2004). Mass spectrometry analysis of Arabidopsis histone H3 reveals distinct combinations of post-translational modifications. Nucleic Acids Res 32, 6511-6518.

Kim, S. C., Sprung, R., Chen, Y., Xu, Y., Ball, H., Pei, J., Cheng, T., Kho, Y., Xiao, H., Xiao, L., et al. (2006). Substrate and functional diversity of lysine acetylation revealed by a proteomics survey. Mol Cell 23, 607-618.

Kouzarides, T. (2007). Chromatin modifications and their function. Cell 128, 693-705. Luo, H., Li, Y., Mu, J. J., Zhang, J., Tonaka, T., Hamamori, Y., Jung, S. Y., Wang, Y., and Qin, J. (2008). Regulation of intra-S phase checkpoint by ionizing radiation (IR)-dependent and IR-independent phosphorylation of SMC3. J Biol Chem 283, 19176-19183.

Margueron, R., Trojer, P., and Reinberg, D. (2005). The key to development: interpreting the histone code? Curr Opin Genet Dev 15, 163-176.

Martin, C., and Zhang, Y. (2007). Mechanisms of epigenetic inheritance. Curr Opin Cell Biol 19, 266-272.

Mersfelder, E. L., and Parthun, M. R. (2006). The tale beyond the tail: histone core domain modifications and the regulation of chromatin structure. Nucleic Acids Res 34, 2653-2662.

Ruthenburg, A. J., Li, H., Patel, D. J., and Allis, C. D. (2007). Multivalent engagement of chromatin modifications by linked binding modules. Nat Rev Mol Cell Biol 8, 983-994.

Sakabe, K., Wang, Z., and Hart, G. W. (2010). Beta-N-acetylglucosamine (O-GlcNAc) is part of the histone code. Proc Natl Acad Sci USA 107, 19915-19920.

Shechter, D., Dormann, H. L., Allis, C. D., and Hake, S. B. (2007). Extraction, purification and analysis of histones. Nat Protoc 2, 1445-1457.

Tateishi, K., Okada, Y., Kallin, E. M., and Zhang, Y. (2009). Role of Jhdm2a in regulating metabolic gene expression and obesity resistance. Nature 458, 757-761.

Wisniewski, J. R., Zougman, A., Kruger, S., and Mann, M. (2007). Mass spectrometric mapping of linker histone H1 variants reveals multiple acetylations, methylations, and phosphorylation as well as differences between cell culture and tissue. Mol Cell Proteomics 6, 72-87.

Wysocka, J., Swigut, T., Milne, T. A., Dou, Y., Zhang, X., Burlingame, A. L., Roeder, R. G., Brivanlou, A. H., and Allis, C. D. (2005). WDR5 associates with histone H3 methylated at K4 and is essential for H3 K4 methylation and vertebrate development. Cell 121, 859-872.

Wysocka, J., Swigut, T., Xiao, H., Milne, T. A., Kwon, S. Y., Landry, J., Kauer, M., Tackett, A. J., Chait, B. T., Badenhorst, P., et al. (2006). A PHD finger of NURF couples histone H3 lysine 4 trimethylation with chromatin remodelling. Nature 442, 86-90.

Zee, B. M., Levin, R. S., Xu, B., LeRoy, G., Wingreen, N. S., and Garcia, B. A. (2010). In vivo residue-specific histone methylation dynamics. J Biol Chem 285, 3341-3350.

Zeng, L., and Zhou, M. M. (2002). Bromodomain: an acetyl-lysine binding domain. FEBS Lett 513, 124-128.

Zhang, J., Chen, Y., Zhang, Z., Xing, G., Wysocka, J., and Zhao, Y. (2010). MS/MS/MS reveals false positive identification of histone serine methylation. J Proteome Res 9, 585-594.

---

What is claimed is:

1. A method of detecting lysine crotonylation as a form of post-translational modification, comprising:
   (a) preparing a mixture of polypeptides from a mammalian sample;
   (b) separating said polypeptides by molecular weight;
   (c) contacting said separated polypeptides with an affinity reagent which binds specifically to a polypeptide containing a crotonyllysine residue; and
   (d) detecting presence of a binding complex between said affinity reagent and one or more of said polypeptides, said presence indicating the existence of lysine crotonylation.

2. The method of claim 1, wherein said separated polypeptides are immobilized on a solid support prior to performing step (c).

3. The method of claim 1, wherein said affinity reagent is immobilized on a solid support prior to performing step (c).

4. The method of claim 1, wherein said affinity reagent binds specifically to histone H2A of which a lysine residue is crotonylated, said lysine residue being lysine 36, lysine 118, lysine 119, or lysine 125 is crotonylated.

5. The method of claim 1, wherein said affinity reagent binds specifically to histone H2B of which a lysine residue is crotonylated, said lysine residue being lysine 5, lysine 11, lysine 12, lysine 15, lysine 16, lysine 20, lysine 23, or lysine 34.

6. The method of claim 1, wherein said affinity reagent binds specifically to histone H3 of which a lysine residue is crotonylated, said lysine residue being lysine 4, lysine 9, lysine 18, lysine 23, lysine 27, or lysine 56.

7. The method of claim 1, wherein said affinity reagent binds specifically to histone H4 of which a lysine residue is crotonylated, said lysine residue being lysine 5, lysine 8, lysine 12, or lysine 16.

8. The method of claim 1, wherein said affinity reagent binds specifically to histone H1 of which a lysine residue is crotonylated, said lysine residue being lysine 33, lysine 63, lysine 84, lysine 89, lysine 96, lysine 158, or lysine 167.

9. The method of claim 1, wherein said affinity reagent binds specifically to a protein of which at least one lysine residue is crotonylated, said protein being selected from the group consisting of H2A, H2B, H3, H2 and H1.

* * * * *

SEQUENCE LISTING

```
<160> NUMBER OF SEQ ID NOS: 13

<210> SEQ ID NO 1
<211> LENGTH: 8
<212> TYPE: PRT
<213> ORGANISM: Artificial Sequence
<220> FEATURE:
<223> OTHER INFORMATION: use as antigen
<220> FEATURE:
<221> NAME/KEY: misc_feature
<222> LOCATION: (6)..(6)
<223> OTHER INFORMATION: Xaa can be any naturally occurring amino acid

<400> SEQUENCE: 1

Cys Gln Leu Ala Thr Xaa Ala Ala
1               5

<210> SEQ ID NO 2
<211> LENGTH: 9
<212> TYPE: PRT
<213> ORGANISM: Artificial Sequence
<220> FEATURE:
<223> OTHER INFORMATION: used as antigen
<220> FEATURE:
<221> NAME/KEY: misc_feature
<222> LOCATION: (4)..(4)
<223> OTHER INFORMATION: Xaa can be any naturally occurring amino acid

<400> SEQUENCE: 2

Cys Tyr Gln Xaa Ser Thr Glu Leu Leu
1               5

<210> SEQ ID NO 3
<211> LENGTH: 11
<212> TYPE: PRT
```

```
<213> ORGANISM: Artificial Sequence
<220> FEATURE:
<223> OTHER INFORMATION: used as a target
<220> FEATURE:
<221> NAME/KEY: misc_feature
<222> LOCATION: (5)..(5)
<223> OTHER INFORMATION: Xaa can be any naturally occurring amino acid

<400> SEQUENCE: 3

Pro Glu Pro Ala Xaa Ser Ala Pro Ala Pro Lys
1               5                   10

<210> SEQ ID NO 4
<211> LENGTH: 228
<212> TYPE: PRT
<213> ORGANISM: human
<220> FEATURE:
<221> NAME/KEY: misc_feature
<222> LOCATION: (2)..(35)
<223> OTHER INFORMATION: Xaa can be any naturally occurring amino acid
<220> FEATURE:
<221> NAME/KEY: misc_feature
<222> LOCATION: (41)..(47)
<223> OTHER INFORMATION: Xaa can be any naturally occurring amino acid
<220> FEATURE:
<221> NAME/KEY: misc_feature
<222> LOCATION: (49)..(53)
<223> OTHER INFORMATION: Xaa can be any naturally occurring amino acid
<220> FEATURE:
<221> NAME/KEY: misc_feature
<222> LOCATION: (55)..(64)
<223> OTHER INFORMATION: Xaa can be any naturally occurring amino acid
<220> FEATURE:
<221> NAME/KEY: misc_feature
<222> LOCATION: (67)..(72)
<223> OTHER INFORMATION: Xaa can be any naturally occurring amino acid
<220> FEATURE:
<221> NAME/KEY: misc_feature
<222> LOCATION: (74)..(82)
<223> OTHER INFORMATION: Xaa can be any naturally occurring amino acid
<220> FEATURE:
<221> NAME/KEY: misc_feature
<222> LOCATION: (84)..(86)
<223> OTHER INFORMATION: Xaa can be any naturally occurring amino acid
<220> FEATURE:
<221> NAME/KEY: misc_feature
<222> LOCATION: (88)..(91)
<223> OTHER INFORMATION: Xaa can be any naturally occurring amino acid
<220> FEATURE:
<221> NAME/KEY: misc_feature
<222> LOCATION: (93)..(104)
<223> OTHER INFORMATION: Xaa can be any naturally occurring amino acid
<220> FEATURE:
<221> NAME/KEY: misc_feature
<222> LOCATION: (109)..(130)
<223> OTHER INFORMATION: Xaa can be any naturally occurring amino acid
<220> FEATURE:
<221> NAME/KEY: misc_feature
<222> LOCATION: (132)..(149)
<223> OTHER INFORMATION: Xaa can be any naturally occurring amino acid
<220> FEATURE:
<221> NAME/KEY: misc_feature
<222> LOCATION: (151)..(169)
<223> OTHER INFORMATION: Xaa can be any naturally occurring amino acid
<220> FEATURE:
<221> NAME/KEY: misc_feature
<222> LOCATION: (171)..(185)
<223> OTHER INFORMATION: Xaa can be any naturally occurring amino acid
<220> FEATURE:
<221> NAME/KEY: misc_feature
<222> LOCATION: (187)..(200)
<223> OTHER INFORMATION: Xaa can be any naturally occurring amino acid
<220> FEATURE:
<221> NAME/KEY: misc_feature
<222> LOCATION: (202)..(225)
<223> OTHER INFORMATION: Xaa can be any naturally occurring amino acid
```

```
<400> SEQUENCE: 4

Ser Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Xaa Xaa Lys Ala Ser Gly Pro Xaa Xaa Xaa Xaa Xaa Lys
        35                  40                  45

Xaa Xaa Xaa Xaa Xaa Lys Xaa Xaa Xaa Xaa Xaa Xaa Xaa Xaa
    50                  55                  60

Lys Lys Xaa Xaa Xaa Xaa Xaa Tyr Xaa Xaa Xaa Xaa Xaa Xaa
65              70                  75                  80

Xaa Xaa Lys Xaa Xaa Lys Xaa Xaa Xaa Lys Xaa Xaa Xaa Xaa
            85                  90                  95

Xaa Xaa Xaa Xaa Xaa Xaa Xaa Lys Leu Asn Lys Xaa Xaa Xaa
            100                 105                 110

Xaa Xaa Xaa Xaa Xaa Xaa Xaa Xaa Xaa Xaa Xaa Xaa Xaa Xaa
        115                 120                 125

Xaa Xaa Lys Xaa Xaa Xaa Xaa Xaa Xaa Xaa Xaa Xaa Xaa Xaa
    130                 135                 140

Xaa Xaa Xaa Xaa Xaa Lys Xaa Xaa Xaa Xaa Xaa Xaa Xaa Xaa
145                 150                 155                 160

Xaa Xaa Xaa Xaa Xaa Xaa Xaa Xaa Lys Xaa Xaa Xaa Xaa Xaa
            165                 170                 175

Xaa Xaa Xaa Xaa Xaa Xaa Xaa Lys Xaa Xaa Xaa Xaa Xaa Xaa
        180                 185                 190

Xaa Xaa Xaa Xaa Xaa Xaa Lys Xaa Xaa Xaa Xaa Xaa Xaa Xaa
    195                 200                 205

Xaa Xaa Xaa Xaa Xaa Xaa Xaa Xaa Xaa Xaa Xaa Xaa Xaa Xaa
        210                 215                 220

Xaa Lys Lys Lys
225

<210> SEQ ID NO 5
<211> LENGTH: 125
<212> TYPE: PRT
<213> ORGANISM: human
<220> FEATURE:
<221> NAME/KEY: misc_feature
<222> LOCATION: (12)..(36)
<223> OTHER INFORMATION: Xaa can be any naturally occurring amino acid
<220> FEATURE:
<221> NAME/KEY: misc_feature
<222> LOCATION: (43)..(81)
<223> OTHER INFORMATION: Xaa can be any naturally occurring amino acid
<220> FEATURE:
<221> NAME/KEY: misc_feature
<222> LOCATION: (89)..(117)
<223> OTHER INFORMATION: Xaa can be any naturally occurring amino acid

<400> SEQUENCE: 5

Ser Gly Arg Gly Lys Gln Gly Gly Lys Ala Arg Xaa Xaa Xaa Xaa
1               5                   10                  15

Xaa Xaa Xaa Xaa Xaa Xaa Xaa Xaa Xaa Xaa Xaa Xaa Xaa Xaa
        20                  25                  30

Xaa Xaa Xaa Xaa Gly Asn Tyr Ser Glu Arg Xaa Xaa Xaa Xaa
        35                  40                  45

Xaa Xaa Xaa Xaa Xaa Xaa Xaa Xaa Xaa Xaa Xaa Xaa Xaa Xaa Xaa
50                  55                  60
```

```
Xaa Xaa Xaa Xaa Xaa Xaa Xaa Xaa Xaa Xaa Xaa Xaa Xaa Xaa Xaa Xaa
65                  70                  75                  80

Xaa His Leu Gln Leu Ala Ile Arg Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa
            100                 105                 110

Xaa Xaa Xaa Xaa Xaa Lys Lys Thr Glu Ser His His Lys
        115                 120                 125

<210> SEQ ID NO 6
<211> LENGTH: 120
<212> TYPE: PRT
<213> ORGANISM: human
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (6)..(10)
<223> OTHER INFORMATION: Xaa can be any naturally occurring amino acid
<220> FEATURE:
<221> NAME/KEY: misc_feature
<222> LOCATION: (24)..(33)
<223> OTHER INFORMATION: Xaa can be any naturally occurring amino acid
<220> FEATURE:
<221> NAME/KEY: misc_feature
<222> LOCATION: (35)..(36)
<223> OTHER INFORMATION: Xaa can be any naturally occurring amino acid
<220> FEATURE:
<221> NAME/KEY: misc_feature
<222> LOCATION: (38)..(45)
<223> OTHER INFORMATION: Xaa can be any naturally occurring amino acid
<220> FEATURE:
<221> NAME/KEY: misc_feature
<222> LOCATION: (47)..(56)
<223> OTHER INFORMATION: Xaa can be any naturally occurring amino acid
<220> FEATURE:
<221> NAME/KEY: misc_feature
<222> LOCATION: (58)..(78)
<223> OTHER INFORMATION: Xaa can be any naturally occurring amino acid
<220> FEATURE:
<221> NAME/KEY: misc_feature
<222> LOCATION: (80)..(82)
<223> OTHER INFORMATION: Xaa can be any naturally occurring amino acid
<220> FEATURE:
<221> NAME/KEY: misc_feature
<222> LOCATION: (86)..(98)
<223> OTHER INFORMATION: Xaa can be any naturally occurring amino acid
<220> FEATURE:
<221> NAME/KEY: misc_feature
<222> LOCATION: (100)..(107)
<223> OTHER INFORMATION: Xaa can be any naturally occurring amino acid
<220> FEATURE:
<221> NAME/KEY: misc_feature
<222> LOCATION: (109)..(115)
<223> OTHER INFORMATION: Xaa can be any naturally occurring amino acid

<400> SEQUENCE: 6

Xaa Xaa Xaa Xaa Lys Xaa Xaa Xaa Xaa Xaa Lys Lys Gly Ser Lys Lys
1               5                   10                  15

Ala Val Thr Lys Ala Gln Lys Xaa Xaa Xaa Xaa Xaa Xaa Xaa Xaa
                20                  25                  30

Xaa Lys Xaa Xaa Tyr Xaa Xaa Xaa Xaa Xaa Xaa Xaa Lys Xaa Xaa
            35                  40                  45

Xaa Xaa Xaa Xaa Xaa Xaa Xaa Lys Xaa Xaa Xaa Xaa Xaa Xaa
        50                  55                  60

Xaa Xaa Xaa Xaa Xaa Xaa Xaa Xaa Xaa Xaa Xaa Xaa Arg Xaa
65                  70                  75                  80
```

Xaa Xaa Tyr Asn Lys Xaa Xaa Xaa Xaa Xaa Xaa Xaa Xaa Xaa
                85                  90                  95

Xaa Xaa Arg Xaa Xaa Xaa Xaa Xaa Xaa Lys Xaa Xaa Xaa Xaa
            100                 105                 110

Xaa Xaa Xaa Lys Ala Val Thr Lys
        115                 120

<210> SEQ ID NO 7
<211> LENGTH: 128
<212> TYPE: PRT
<213> ORGANISM: human
<220> FEATURE:
<221> NAME/KEY: misc_feature
<222> LOCATION: (10)..(13)
<223> OTHER INFORMATION: Xaa can be any naturally occurring amino acid
<220> FEATURE:
<221> NAME/KEY: misc_feature
<222> LOCATION: (15)..(17)
<223> OTHER INFORMATION: Xaa can be any naturally occurring amino acid
<220> FEATURE:
<221> NAME/KEY: misc_feature
<222> LOCATION: (19)..(22)
<223> OTHER INFORMATION: Xaa can be any naturally occurring amino acid
<220> FEATURE:
<221> NAME/KEY: misc_feature
<222> LOCATION: (28)..(35)
<223> OTHER INFORMATION: Xaa can be any naturally occurring amino acid
<220> FEATURE:
<221> NAME/KEY: misc_feature
<222> LOCATION: (37)..(55)
<223> OTHER INFORMATION: Xaa can be any naturally occurring amino acid
<220> FEATURE:
<221> NAME/KEY: misc_feature
<222> LOCATION: (57)..(62)
<223> OTHER INFORMATION: Xaa can be any naturally occurring amino acid
<220> FEATURE:
<221> NAME/KEY: misc_feature
<222> LOCATION: (64)..(78)
<223> OTHER INFORMATION: Xaa can be any naturally occurring amino acid
<220> FEATURE:
<221> NAME/KEY: misc_feature
<222> LOCATION: (80)..(121)
<223> OTHER INFORMATION: Xaa can be any naturally occurring amino acid

<400> SEQUENCE: 7

Ala Arg Thr Lys Gln Thr Ala Arg Lys Xaa Xaa Xaa Xaa Lys Xaa Xaa
1               5                   10                  15

Xaa Lys Xaa Xaa Xaa Xaa Lys Ala Ala Arg Lys Xaa Xaa Xaa Xaa Xaa
            20                  25                  30

Xaa Xaa Xaa Lys Xaa Xaa Xaa Xaa Xaa Xaa Xaa Xaa Xaa Xaa Xaa Xaa
        35                  40                  45

Xaa Xaa Xaa Xaa Xaa Xaa Lys Xaa Xaa Xaa Xaa Xaa Arg Xaa
    50                  55                  60

Xaa Xaa Xaa Xaa Xaa Xaa Xaa Xaa Xaa Xaa Xaa Xaa Lys Xaa
65                  70                  75                  80

Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Lys Asp Ile Gln Leu Ala Arg
        115                 120                 125

<210> SEQ ID NO 8
<211> LENGTH: 91
<212> TYPE: PRT
<213> ORGANISM: human
<220> FEATURE:

```
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(11)
<223> OTHER INFORMATION: Xaa can be any naturally occurring amino acid
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (21)..(30)
<223> OTHER INFORMATION: Xaa can be any naturally occurring amino acid
<220> FEATURE:
<221> NAME/KEY: misc_feature
<222> LOCATION: (32)..(34)
<223> OTHER INFORMATION: Xaa can be any naturally occurring amino acid
<220> FEATURE:
<221> NAME/KEY: misc_feature
<222> LOCATION: (36)..(50)
<223> OTHER INFORMATION: Xaa can be any naturally occurring amino acid
<220> FEATURE:
<221> NAME/KEY: misc_feature
<222> LOCATION: (56)..(58)
<223> OTHER INFORMATION: Xaa can be any naturally occurring amino acid
<220> FEATURE:
<221> NAME/KEY: misc_feature
<222> LOCATION: (60)..(66)
<223> OTHER INFORMATION: Xaa can be any naturally occurring amino acid
<220> FEATURE:
<221> NAME/KEY: misc_feature
<222> LOCATION: (68)..(76)
<223> OTHER INFORMATION: Xaa can be any naturally occurring amino acid
<220> FEATURE:
<221> NAME/KEY: misc_feature
<222> LOCATION: (80)..(87)
<223> OTHER INFORMATION: Xaa can be any naturally occurring amino acid

<400> SEQUENCE: 8

Ser Gly Arg Gly Lys Xaa Xaa Lys Xaa Xaa Xaa Lys Xaa Xaa Xaa Lys
1               5                   10                  15

Arg His Arg Lys Xaa Xaa Xaa Xaa Xaa Xaa Xaa Xaa Xaa Lys Xaa
            20                  25                  30

Xaa Xaa Arg Xaa Xaa Xaa Xaa Xaa Xaa Xaa Xaa Xaa Xaa Xaa Xaa
        35                  40                  45

Xaa Xaa Tyr Glu Glu Thr Arg Xaa Xaa Xaa Lys Xaa Xaa Xaa Xaa Xaa
    50                  55                  60

Xaa Xaa Arg Xaa Xaa Xaa Xaa Xaa Xaa Xaa Xaa Lys Arg Lys Xaa
65                  70                  75                  80

Xaa Xaa Xaa Xaa Xaa Xaa Xaa Tyr Ala Leu Lys
                85                  90

<210> SEQ ID NO 9
<211> LENGTH: 129
<212> TYPE: PRT
<213> ORGANISM: human
<220> FEATURE:
<221> NAME/KEY: misc_feature
<222> LOCATION: (18)..(32)
<223> OTHER INFORMATION: Xaa can be any naturally occurring amino acid
<220> FEATURE:
<221> NAME/KEY: misc_feature
<222> LOCATION: (40)..(112)
<223> OTHER INFORMATION: Xaa can be any naturally occurring amino acid

<400> SEQUENCE: 9

Ser Gly Arg Gly Lys Gln Gly Gly Lys Ala Arg Ala Lys Ala Lys Thr
1               5                   10                  15
```

-continued

Arg Xaa Xaa Xaa Xaa Xaa Xaa Xaa Xaa Xaa Xaa Xaa Xaa
    20                  25                  30

Leu Leu Arg Lys Gly Asn Tyr Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
 50                  55                  60

Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa
             85                  90                  95

Xaa Xaa Xaa Xaa Xaa Xaa Xaa Xaa Xaa Xaa Xaa Xaa Xaa Xaa Xaa
            100                 105                 110

Ala Val Leu Leu Pro Lys Lys Thr Glu Ser His His Lys Ala Lys Gly
        115                 120                 125

Lys

<210> SEQ ID NO 10
<211> LENGTH: 125
<212> TYPE: PRT
<213> ORGANISM: human
<220> FEATURE:
<221> NAME/KEY: misc_feature
<222> LOCATION: (25)..(30)
<223> OTHER INFORMATION: Xaa can be any naturally occurring amino acid
<220> FEATURE:
<221> NAME/KEY: misc_feature
<222> LOCATION: (40)..(118)
<223> OTHER INFORMATION: Xaa can be any naturally occurring amino acid

<400> SEQUENCE: 10

Pro Glu Pro Ala Lys Ser Ala Pro Ala Pro Lys Lys Gly Ser Lys Lys
1               5                   10                  15

Ala Val Thr Lys Ala Gln Lys Lys Xaa Xaa Xaa Xaa Xaa Xaa Arg Ser
            20                  25                  30

Arg Lys Glu Ser Tyr Ser Ile Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
 50                  55                  60

Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa
             85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Thr Lys Tyr Thr Ser Ser Lys
        115                 120                 125

<210> SEQ ID NO 11
<211> LENGTH: 134
<212> TYPE: PRT
<213> ORGANISM: human
<220> FEATURE:
<221> NAME/KEY: misc_feature
<222> LOCATION: (29)..(52)
<223> OTHER INFORMATION: Xaa can be any naturally occurring amino acid
<220> FEATURE:
<221> NAME/KEY: misc_feature
<222> LOCATION: (59)..(127)
<223> OTHER INFORMATION: Xaa can be any naturally occurring amino acid

<400> SEQUENCE: 11

```
Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Xaa Xaa Arg Tyr Gln Lys Ser Thr Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa Xaa Xaa Xaa Xaa Arg
    115                 120                 125

Ile Arg Gly Glu Arg Ala
        130
```

```
<210> SEQ ID NO 12
<211> LENGTH: 104
<212> TYPE: PRT
<213> ORGANISM: human
<220> FEATURE:
<221> NAME/KEY: misc_feature
<222> LOCATION: (29)..(97)
<223> OTHER INFORMATION: Xaa can be any naturally occurring amino acid

<400> SEQUENCE: 12

Ser Gly Arg Gly Lys Gly Gly Lys Gly Leu Gly Lys Gly Gly Ala Lys
1               5                   10                  15

Arg His Arg Lys Val Leu Arg Asp Asn Ile Gln Gly Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
            85                  90                  95

Xaa Thr Leu Tyr Gly Phe Gly Gly
        100
```

```
<210> SEQ ID NO 13
<211> LENGTH: 212
<212> TYPE: PRT
<213> ORGANISM: human
<220> FEATURE:
<221> NAME/KEY: misc_feature
<222> LOCATION: (4)..(30)
<223> OTHER INFORMATION: Xaa can be any naturally occurring amino acid
<220> FEATURE:
<221> NAME/KEY: misc_feature
<222> LOCATION: (38)..(59)
<223> OTHER INFORMATION: Xaa can be any naturally occurring amino acid
<220> FEATURE:
<221> NAME/KEY: misc_feature
<222> LOCATION: (66)..(83)
<223> OTHER INFORMATION: Xaa can be any naturally occurring amino acid
<220> FEATURE:
<221> NAME/KEY: misc_feature
```

```
<222> LOCATION: (98)..(155)
<223> OTHER INFORMATION: Xaa can be any naturally occurring amino acid
<220> FEATURE:
<221> NAME/KEY: misc_feature
<222> LOCATION: (160)..(162)
<223> OTHER INFORMATION: Xaa can be any naturally occurring amino acid
<220> FEATURE:
<221> NAME/KEY: misc_feature
<222> LOCATION: (171)..(210)
<223> OTHER INFORMATION: Xaa can be any naturally occurring amino acid

<400> SEQUENCE: 13

Ser Glu Thr Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Pro Arg
            20                  25                  30

Lys Ala Ser Gly Pro Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Ala Leu Lys Lys Ala
            50                  55                  60

Leu Xaa Xaa Xaa Xaa Xaa Xaa Xaa Xaa Xaa Xaa Xaa Xaa Xaa Xaa
65                  70                  75                  80

Xaa Xaa Xaa Lys Ser Leu Val Ser Lys Gly Thr Leu Val Gln Thr Lys
            85                  90                  95

Gly Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Xaa Xaa Xaa Xaa Xaa Xaa Xaa
            130                 135                 140

Xaa Xaa Xaa Xaa Xaa Xaa Xaa Xaa Xaa Lys Ala Lys Lys Xaa
145                 150                 155                 160

Xaa Xaa Ala Thr Val Thr Lys Lys Val Ala Xaa Xaa Xaa Xaa Xaa
            165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
            195                 200                 205

Xaa Xaa Lys Lys
    210
```